US009200289B1

(12) United States Patent
Bermudes

(10) Patent No.: US 9,200,289 B1
(45) **Date of Patent: *Dec. 1, 2015**

(54) PROTEASE INHIBITOR: PROTEASE SENSITIVITY EXPRESSION SYSTEM AND METHOD IMPROVING THE THERAPEUTIC ACTIVITY AND SPECIFICITY OF PROTEINS AND PHAGE AND PHAGEMIDS DELIVERED BY BACTERIA

(71) Applicant: David Gordon Bermudes, Woodland Hills, CA (US)

(72) Inventor: David Gordon Bermudes, Woodland Hills, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/135,003

(22) Filed: Dec. 19, 2013

Related U.S. Application Data

(62) Division of application No. 13/562,488, filed on Jul. 31, 2012, now Pat. No. 8,623,350, which is a division of application No. 12/703,158, filed on Feb. 9, 2010, now Pat. No. 8,241,623.

(60) Provisional application No. 61/151,019, filed on Feb. 9, 2009.

(51) Int. Cl.

| | |
|---|---|
| ***A61K 35/74*** | (2015.01) |
| ***C12N 15/74*** | (2006.01) |
| ***C12N 9/22*** | (2006.01) |
| ***C07K 14/81*** | (2006.01) |
| ***C12N 9/02*** | (2006.01) |
| ***C07K 14/005*** | (2006.01) |
| ***C07K 14/245*** | (2006.01) |
| ***C12N 15/113*** | (2010.01) |
| *A61K 38/16* | (2006.01) |
| *A61K 38/55* | (2006.01) |

(52) U.S. Cl.
CPC .............. *C12N 15/74* (2013.01); *C07K 14/005* (2013.01); *C07K 14/245* (2013.01); *C07K 14/81* (2013.01); *C12N 9/0071* (2013.01); *C12N 9/22* (2013.01); *C12N 15/1135* (2013.01); *A61K 35/74* (2013.01); *A61K 38/164* (2013.01); *A61K 38/55* (2013.01)

(58) Field of Classification Search
CPC ..... A61K 35/74; A61K 38/164; A61K 38/55; C12N 15/74
See application file for complete search history.

(56) References Cited

U.S. PATENT DOCUMENTS

| | | | |
|---|---|---|---|
| 6,080,849 | A | 6/2000 | Bermudes et al. |
| 6,190,657 | B1 | 2/2001 | Pawelek et al. |
| 6,447,784 | B1 | 9/2002 | Bermudes et al. |
| 6,475,482 | B1 | 11/2002 | Bermudes et al. |
| 6,548,287 | B1 | 4/2003 | Powell et al. |
| 6,685,935 | B1 | 2/2004 | Pawelek et al. |
| 6,863,894 | B2 | 3/2005 | Bermudes et al. |
| 6,923,972 | B2 | 8/2005 | Bermudes et al. |
| 6,962,696 | B1 | 11/2005 | Bermudes et al. |
| 7,354,592 | B2 | 4/2008 | Bermudes et al. |
| 7,390,646 | B2 | 6/2008 | Andino-Pavlovsky et al. |
| 7,452,531 | B2 | 11/2008 | Bermudes et al. |
| 8,241,623 | B1 | 8/2012 | Bermudes |
| 8,623,350 | B1 | 1/2014 | Bermudes |
| 2003/0059400 | A1 | 3/2003 | Szalay |
| 2008/0311081 | A1 | 12/2008 | Fruehauf et al. |
| 2009/0123426 | A1 | 5/2009 | Li et al. |

FOREIGN PATENT DOCUMENTS

| | | |
|---|---|---|
| EP | 0973911 | 1/2000 |
| EP | 1655370 | 5/2006 |
| WO | WO9714782 | 4/1997 |
| WO | WO9910014 | 3/1999 |
| WO | WO9910485 | 3/1999 |
| WO | WO0004919 | 2/2000 |
| WO | WO0114579 | 3/2000 |
| WO | WO2004076484 | 9/2004 |
| WO | WO2005018332 | 3/2005 |
| WO | WO2006116545 | 11/2006 |
| WO | WO2008091375 | 7/2008 |
| WO | WO2009086116 | 7/2009 |

*Primary Examiner* — J. E. Angell
(74) *Attorney, Agent, or Firm* — Steven M. Hoffberg, Esq.; Ostrolenk Faber LLP

(57) ABSTRACT

The present invention uses co-expression of protease inhibitors and protease sensitive therapeutic agents that results in their localized production within the target tissue and inactivation outside of the target tissue, thereby increasing therapeutic activity and reducing the systemic toxicity. Inactivation is also accomplished by engineering protease degradation sites within the therapeutic construct for proteases, preferably those that are under-expressed within the target tissue yet present in non-target tissues within the body, resulting in therapeutic activity within the target tissue and inactivation outside of the target tissue. Novel chimeric proteins secreted by bacteria are also described. The chimeric proteins include chimeric toxins targeted to neoplastic cells and cells of the immune system. Novel combination therapies of these protease inhibitor:chimeric toxin-expressing bacteria together with small-molecule and biologic agents are also described. Non-conjugative bacteria capable of delivering phage/phagemids expression cassettes for DNA and RNA-based therapeutics are also described.

20 Claims, 7 Drawing Sheets

1 18
M13 pIII SS 18aa
Targeting TGFγ mature 50aa
19 372
M13 pIII
Col E3 C-term 1 18
M13 pIII
Lytic peptide
TGFγ (targeting)
19 372
M13 pIII
Col E3 C-term 1 18
M13 pIII
TGFγ (targeting)
19 372
M13 pIII
444 576
Col E7 C-term 1 18
M13 pIII
Lytic peptide
TGFγ (targeting)
19 372
M13 pIII
444 576
Col E7 C-term 1 18
M13 pIII
TGFγ (targeting)
19 372
M13 pIII
450 626
Col Ia C-term 1 18
M13 pIII
Lytic peptide
TGFγ (targeting)
19 372
M13
450 626
Col Ia C-term Hly CABD from E. Coli Hx CABD from Actinobacillus Hybrid CABD from E. Coli and Actinobacillus Hybrid CABD from E. Coli and Actinobacillus with a chimeric A which has the C-terminus of the E. coli A

PROTEASE INHIBITOR: PROTEASE SENSITIVITY EXPRESSION SYSTEM AND METHOD IMPROVING THE THERAPEUTIC ACTIVITY AND SPECIFICITY OF PROTEINS AND PHAGE AND PHAGEMIDS DELIVERED BY BACTERIA

CROSS REFERENCE TO RELATED APPLICATIONS

The present application is a Continuation of U.S. patent application Ser. No. 13/562,488, filed Jul. 31, 2012, now U.S. Pat. No. 8,623,350, issued Dec. 31, 2013, which is a Division of U.S. patent application Ser. No. 12/703,158, filed Feb. 9, 2010, now U.S. Pat. No. 8,241,623, issued Aug. 14, 2012, which is a non-provisional of U.S. Provisional Patent Application Ser. No. 61/151,019, filed Feb. 9, 2009, each or which is expressly incorporated herein by reference.

1. BACKGROUND OF THE INVENTION 1.1. Field of the Invention

This invention is generally in the field of therapeutic delivery systems, systems and methods for providing co-expression of protease inhibitors with genetically engineered protease sensitive therapeutic constructs, and chimeric proteins.

1.2. Relevant Art

Citation or identification of any reference herein, or any section of this application shall not be construed as an admission that such reference is available as prior art to the present application.

Tumor-targeted bacteria offer tremendous potential advantages for the treatment of solid tumors, including the targeting from a distant inoculation site and the ability to express therapeutic agents directly within the tumor. However, the primary shortcoming of tumor-targeted bacteria investigated in the human clinical trials (*Salmonella* strain VNP20009 and its derivative TAPET-CD) is that no significant antitumor activity was observed, even in patients where the bacteria was documented to target the tumor. One method of increasing the ability of the bacteria to kill tumor cells is to engineer the bacteria to express conventional bacterial toxins, but this approach poses risks of systemic toxicity. See, e.g., U.S. Pat. Nos. 7,452,531, 7,354,592, 6,962,696, 6,923,972, 6,863,894, 6,685,935, 6,475,482, 6,447,784, 6,190,657, 6,080,849 and US Pub. 2003/0059400, each of which is expressly incorporated herein by reference. These patents disclose, inter alia, pharmaceutical formulations and methods of administration to humans and animals, useful in conjunction with the present technique.

Use of protein toxins for treatment of various disorders including inflammation, autoimmunity, neurological disorders and cancer has long-suffered from off-target toxicity. Some toxins have a natural degree of specificity for their target, such as botulinum toxin which is specific for neurons. Toxin specificity has been achieved by attachment of a specific antibodies or peptide ligands (e.g., *Pseudomonas* endotoxin A (PE-ToxA) antibody conjugate, known as an immunotoxin). Based upon the binding specificity of the attached antibody moiety for a specific target, enhanced specificity of the target is achieved. Other toxins have been engineered to achieve specificity based upon their sight of activation. For example, aerolysin requires proteolytic activation to become cytotoxic. Substitution of the natural protease cleavage site for a tumor-specific protease cleavage site (e.g., that of the PSA protease or urokinase) results in a toxin selectively activated within tumors. However, in both these types of engineered toxins, off-target toxicity can occur. In the case of the *Pseudomonas* immunotoxin, several dose-limiting toxicities have been identified. Vascular leakage syndrome (VLS) is associated with hypoalbuminemia, edema, weight gain, hypotension and occasional dyspnea, which is suggested to occur by immunotoxin-mediated endothelial cell injury (Baluna et al., 2000, Exp. Cell Res. 258: 417-424), resulting in a dose-limiting toxicity. Renal injury has occurred in some patients treated with immunotoxins, which may be due to micro-aggregates of the immunotoxin (Frankel et al., 2001, Blood 98: 722a). Liver damage from immunotoxins is a frequent occurrence that is believed to be multifactorial (Frankel, 2002, Clinical Cancer Research 8: 942-944). To date, antibodies with proteinaceous toxins have limited success clinically. One explanation for the off target toxicity is that although a specific agent is targeted to the tumor and/or specifically activated there, the agent is also toxic if it diffuses out of the tumor, which is likely to occur due to the high osmotic pressure that occurs within tumors (Jain, R. K., 1994, Barriers to drug delivery in solid tumors, Scientific American 271 (11): 58-65). Once activated inside the tumor and diffused back outside, toxins such as aerolysin remain active and are able to contribute to non-target toxicity.

Another method of increasing the therapeutic activity of tumor-targeted bacteria is to use F' *Salmonella* for the purpose of liberating filamentous phage within the tumor that are capable of delivering genetic material to tumor cells (See, WO/2001/014579, expressly incorporated herein by reference). However, the presence of the F' factor in those studies is known to enhance the genetic exchange of the *Salmonella* with other bacteria such as *E. coli*, and therefore poses risks of releasing genes into the environment that could enhance the pathogenic potential of other bacteria. Moreover, no antitumor activity was demonstrated.

2. SUMMARY OF THE INVENTION

A Protease Inhibitor: Protease Sensitivity Expression System Improving the Therapeutic Specificity The present invention consists of the co-expression by the expression system, or a combination of expression systems, of a protease inhibitor together with a protease sensitive therapeutic agent. Within the local high-concentration of the targeted tissue or cells such as a tumor environment, the protease inhibitor prevents the degradation of the agent, which is therapeutically active against the target tissue such as a tumor. Upon egress from the confined space of the targeted tissue such as the tumor, the inhibitor falls below the inhibitory concentration, and the therapeutic agent is freely degraded, resulting in cell or tissue-specific activity and non-target cell or tissue inactivity (Table I). A schematic diagram illustrating the effect of co-expression is shown in FIGS. 1A and 1B.

TABLE 1

Relative effect of toxin forms with and without protease sensitivity and protease inhibitor.

| Composition | Tumor Efficacy | Systemic Toxicity |
|---|---|---|
| Protease activated and/or insensitive toxin | +++ | ++ |
| Protease sensitive toxin | + | − |
| Protease sensitive toxin + protease inhibitor | +++++ | − |

The therapeutic agent can be a peptide or protein, toxin, chimeric toxin, cytokine, antibody, biospecific antibody including single chain antibodies, chemokine, prodrug converting enzyme or phage/phagemid. In a preferred embodiment the therapeutic agent is a toxin, or modified toxin. In another preferred embodiment, the therapeutic agent is a phage or phagemid capable of delivering DNA or RNA.

Toxins useful in conjunction with the present invention that can be modified uniquely to suit the delivery by a bacterium and may be further engineered to have tumor-selective targeting include, azurin, carboxyesterase Est55 (a prodrug converting enzyme from *Geobacillus* that activates CPT-11 to SN-38), *Bacillus* sp. cytolysins, cytolethal distending toxin (cldt), typhoid toxin (pltAB), cldt:plt hybrids, cytotoxic necrotic factor (cnf), dermonecrotic factor (dnf), shiga toxin and shiga-like toxins, colicins including colicin E492, colE3, colE7 and col-Ia, membrane lytic peptides from *Staphalococcus* (listed below), bacterial collegenases (e.g., that from *Salmonella* strain DT104, see WO/2005/018332, the entirety of which is expressly incorporated herein by reference), repeat in toxin (RTX) family members (together with the necessary acylation and secretion genes) including *Actinobacillus* leucotoxin, a leuckotoxin:*E. coli* HlyA hybrid, *E. coli* HlyA hemolysin, and *Bordetella* adenylate cyclase toxin, heat stable enterotoxins from *E. coli* and *Vibrio* sp., autotransporter toxins including picU espC, and sat, chlostridium enterotoxin, aerolysin, subtilase, saporin, ricin, pertussus toxin, and porB.

The toxin may be further modified by addition of one or more protease cleavage sites that enhance its degradation outside of the tumor. Preferred protease cleavage sites are those for proteases that are under-expressed within the tumor compared to normal tissues (rather than over-expressed within the tumor as utilized for aerolysin activation). However, the expression levels of many proteases are elevated within tumors. Proteases for which inhibitory peptides may be expressed include furin, tissue plasminogen activator, activated protein C, factor Xa, granzymes (A, B & M), cathepsins (A, B, C, D, E, F, G, H, K, L, S, W & X), thrombin, plasmin, urokinase, matrix metaloproteaes, prostate specific antigen (PSA) and kallikrein 2.

Furin recognizes a number of specific cleavage sites, including RXRAKR↓ SEQ ID NO:57. In accordance with the present invention, the presence of this cleavage site, whether naturally occurring or introduced through genetic modification, may be compensated for within the target tissue by co-expression of a furin inhibitor, stabilizing its activity unless it escapes the target tissue such as a tumor. Use of protease inhibitors alone or in combination by bacterial delivery vectors has not previously been suggested. Indeed, Wang et al. 2008 suggested furin inhibitors could be used as antibiotics to suppress bacterial infection which would thereby interfere with delivery by a bacterial vector. Therefore, it has not been considered desirable to use a furin inhibitor or other protease inhibitors to have a positive effect on the bacteria and/or the therapeutics they release.

The peptide inhibitors are engineered to be secreted from the bacteria secretion signals known to those skilled in the arts, including ompA, OmpF, M13pIII, cldt N-terminal signal sequences or hlyA C-terminal signal sequence (requires addition of hlyBD and TolC). The inhibitors can be further modified to have the protease cleavage signal of the protease that they inhibit or for a different protease. Multiple protease inhibitor sequences may alternate between protease cleavage sequences or recognition sites.

Chimeric toxins may be further modified by the addition of known cell penetrating (ferry) peptide which further improves their entry into target cells. Cell penetrating peptides include those derived from the HIV TAT protein, the antennapedia homeodomain (penetraxin), Kaposi fibroblast growth factor (FGF) membrane-translocating sequence (MTS), herpes simplex virus VP22, hexahistidine, hexalysine, or hexaarginine.

The present invention also provides in accordance with some embodiments, unique chimeric modifications of the above listed toxins that contain specific combinations of components resulting in secretion by and gram-negative bacteria (e.g., *Salmonella, Shigella, E. coli*) and selective anti-tumor activity. The invention also provides protease sensitivity (deactivation) which may include the addition of protease cleavage sites and may be co-expressed with a protease inhibitor. The chimeric proteins may have one or more additional features or protein domains known to those skilled in the arts which are designed to 1) be active or catalytic domains that result in the death of the cell or make them susceptible to other known anticancer agents, 2) allow or facilitate them being secreted or released by autolytic peptides such as colicin release peptides, 3) membrane protein transduction (ferry) peptides, 4) autotransporter domains, 5) have targeting peptides that direct them to the target cells, and 6) protease cleavage sites for activation (e.g., release from parent peptide). However, the specific organization and combination of these domains is unique and specific to the invention.

Bombesin and gastrin are amidated peptides. Amidation of these peptides would not be expected to occur in bacteria. A unique composition in accordance with one embodiment of the present invention is the co-expression of the C-terminal amidating enzyme, which results in amidating these peptides in order for them to confer their targeting specificity.

Small lytic peptides (less than 50 amino acids) are used to construct chimeric proteins for more than one purpose. The chimeric proteins containing lytic peptides may be directly cytotoxic for the cancer cells, and/or other cells of the tumor including the tumor matrix cells and immune cells which may diminish the effects of the bacteria by eliminating them. Furthermore, the lytic peptides are useful in chimeric proteins for affecting release from the endosome. Small lytic peptides have been used in the experimental treatment of cancer. However, it is evident that most, if not all, of the commonly used antitumor small lytic peptides have strong antibacterial activity, and thus are not compatible with delivery by a bacterium (see Table 1 of Leschner and Hansel, 2004 Current Pharmaceutical Design 10: 2299-2310, the entirety of which is expressly incorporated herein by reference). Small lytic peptides useful in the invention are those derived from *Staphylococcus aureus, S. epidermidis* and related species, including the phenol-soluble modulin (PSM) peptides and delta-lysin (Wang et al., 2007 Nature Medicine 13: 1510-1514, expressly incorporated herein by reference). The selection of the lytic peptide depends upon the primary purpose of the construct, which may be used in combination with other constructs providing other anticancer features. Construct designed to be directly cytotoxic to cells employ the more cytoxic peptides, particularly PSM-$\alpha$-3. Constructs which are designed to use the lytic peptide to affect escape from the endosome se the peptides with the lower level of cytotoxicity, such as PSM-alpha-1, PSM-alpha-2 or delta-lysin.

2.2 Non-Conjugative, Bacteria Capable of Delivering DNA and RNA Interference (RNAi) Mediated by Small Interfering RNAs (siRNA) and/or microRNAs (miRNA).

The present invention provides, according to some embodiments, a composition that would minimize the effect of bacteria released into the environment by eliminating the ability of the bacteria to exchange genetic information with related bacteria, as well as provide a delivery enhancing bacteria resulting in a greater therapeutic effect. Conjugative transfer is a major genetic exchange mechanism that may occur between *Salmonella* and the normal commensal gut bacterium *E. coli*, requiring the presence of an F' factor. The present invention provides gram-negative bacteria including *E. coli, Vibrio, Shigella* and *Salmonella* that are genetically modified in one or more ways to eliminate conjugative transfer of DNA with closely related species including *E. coli*. One of the modifications works on both male (F'+) and female (F'−) bacteria. These modifications facilitate the safety of a bacteria carrying phage capable of delivering DNA or small interfering RNA (siRNA) or microRNA (miRNA) molecules that mediate RNA interference (RNAi), as well as for bacteria expressing chimeric toxins. The phage/phagemids may be further modified to express membrane lytic peptides enhancing their release from the endosome. See, e.g., U.S. Pat. No. 7,390,646, US 2008/0311081, 2009/0123426, WO 2008/091375, WO 1999/010485, WO 1999/010014, WO 2009/086116, each of which is expressly incorporated herein by reference it its entirety MicroRNAs (miRNA) are single-stranded RNA molecules of, for example, about 21-23 nucleotides in length, which regulate gene expression. miRNAs are encoded by genes from whose DNA they are transcribed but miRNAs are not translated into protein (non-coding RNA; instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

Small interfering RNA (siRNA), sometimes known as short interfering RNA or silencing RNA, is a class of 19-25 nucleotide-long double-stranded RNA molecules with 3" overhangs. Asymmetric interfering RNAs have 3" and 5" antisense overhangs and may be only 15 base pairs in length (Sun et al. 2008 Nature Biotechnology 26: 1379-1382, incorporated in its entirety herein). Interfering RNAs play a variety of roles in biology. Most notably, siRNA is involved in the RNA interference (RNAi) pathway, where it interferes with the expression of a specific gene. In addition to their role in the RNAi pathway, siRNAs also act in RNAi-related pathways, e.g., as an antiviral mechanism or in shaping the chromatin structure of a genome.

The bacterial strains according to various aspects of the invention useful for delivery of phage/phagemids especially include any of those expressing protease inhibitors, and/or chimeric toxins. The bacteria may also be modified variously in order to accommodate the production of the phage such that they are stably maintained and released from the bacteria. These modifications may include: introduction of an F' pilus factor which allows the filamentous phage to infect the bacteria, a "helper phage" which provides phage genes and functions in trans necessary to package a phagemid, a phagemid containing a modified phage coat protein (e.g., pIII, pVIII) into which a targeting ligand is inserted, and phagemid effector genes, which may include eukaryotic promoters for tumor cell expression of anticancer genes, or genes that are transcribed into short hairpin RNAs that function as interfering RNA molecules (RNAi). More than one gene and/or siRNA and/or miRNA may be expressed from a single phagemid and may employ ribosomal reentry signals (RESs). A preferred bacterial phagemid with eukaryotic expression components (including an SV40 origin of replication, HSV-TK polyadenylation signal, a CVM IE promoter and an SV40 polyadenylation signal) is pEGFP-N1. The siRNA and/or miRNA molecules may utilize the T7 promoter. Constructs using the T7 promoter may contain one or more copies of the T7 polymerase under control of a eukaryotic promoter, which, when transcribed and translated, is capable of expressing the siRNA and/or miRNA constructs under control of the T7 promoter.

The phagmid-expressed genes may serve multiple purposes. The phagemid genes may serve to suppress certain immune responses within the tumor, including T-cells, macrophages and neutrophils that may limit the ability of the bacteria to effectively reach all the tumor cells within a tumor. The phagmid genes may also serve to directly inhibit tumor cells, either through the expression of anti-tumor genes (e.g., tumor suppressor genes such as p53) or by generating siRNA and/or miRNA or other RNAi molecules, which suppress the presence of mRNA transcripts, suppressing the neoplastic genes such as KRAS.

The F' pilus factors are provided by the F' plasmid, and are needed for phage to be able to infect a bacterial cell. The F' factor provides other functions which may be undesirable in conjunction with aspects of the present invention, including mating stabilization and DNA transfer. The present invention therefore provides, according to one aspect, a composition lacking these features by their genetic disruption on the F' factor or by the cloning of the pilus factor genes into the tumor-targeted bacterium in the absence of the other factors, and hence, resulting in a strain which is non-conjugative and significantly less likely to transfer DNA to other bacteria. The invention may also incorporate entry exclusion into the bacteria and the fertility inhibition complex (finO and finP), and thus, even in tumor-targeted bacterial strains in which the pilus factors are not incorporated (i.e., F−), the bacterial strain will remain resistant to mating with F' bacteria.

3. OBJECTS OF THE INVENTION

The present invention provides, according to one embodiment, improved live attenuated therapeutic bacterial strains that express one or more therapeutic molecules together with one or more protease inhibitor polypeptides that inhibit local proteases that could deactivate the therapeutic molecules. In particular, one aspect of the invention relates to live attenuated tumor-targeted bacterial strains that may include *Salmonella* vectoring chimeric anti-tumor toxins to an individual to elicit a therapeutic response against cancer. Another aspect of the invention relates to live attenuated tumor-targeted bacterial strains that may include *Salmonella* vectoring filamentous phage that encode anti-tumor DNA and RNA molecules to an individual to elicit a therapeutic response against cancer including cancer stem cells. The filamentous phage may also be targeted to tumor matrix cells, and immune cells.

Whereas the prior strains of *Salmonella* studied in human clinical trails used either no heterologous antitumor protein (i.e., VNP20009) or an antitumor protein located within the cytoplasm of the bacterium (i.e., cytosine deaminase expressed by TAPET-CD), the invention provides, according to some embodiments, methods and compositions comprising bacterial vectors that secrete protease inhibitors that protect coexpressed protease sensitive antitumor molecules that are also secreted into the tumor for the treatment of cancer.

The bacteria according to a preferred embodiment of the present invention have little or no ability to undergo bacterial conjugation, limiting incoming and outgoing exchange of genetic material, whereas the prior art fails to limit exchange of genetic material. In addition, certain of the therapeutic molecules have co-transmission requirements that are distal to the therapeutic molecule location further limiting known forms of genetic exchange.

Aspects of the present invention also provide novel chimeric bacterial toxins particularly suited for expression by gram-negative bacteria. The toxins may have added targeting ligands that render them selectively cytotoxic for tumor cells, tumor stem cells and/or matrix and tumor-infiltrating immune cells. The invention also provides means to determine optimal toxin combinations which are preferably additive or more preferably synergistic. The invention also provides means to determine the optimal combination of protein toxin with conventional cancer chemotherapeutics or biologics. Accordingly, administration to an individual, of a live *Salmonella* bacterial vector, in accordance with an aspect of the present invention, that is genetically engineered to express one or more protease inhibitors as described herein co-expressed with one or more cytotoxic proteins has the ability to establish a population in the tumor, kill tumor cells, tumor stem cells as well as tumor matrix and immune infiltrating cells, resulting in a therapeutic benefit.

A preferred composition will contain, for example, a sufficient amount of live bacteria expressing the protease inhibitors and cytotoxin(s) to produce a therapeutic response in the patient. Accordingly, the attenuated *Salmonella* strains described herein are both safe and useful as live bacterial vectors that can be orally administered to an individual to provide therapeutic benefit for the treatment of cancer.

Although not wishing to be bound by any particular mechanism, an effective antitumor response in humans by administration of genetically engineered, attenuated strains of *Salmonella* strains as described herein may be due to the ability of such mutant strains to persist in the tumor and to supply their own nutrient needs by killing tumor cells and further expanding the zone of the tumor that they occupy. Bacterial strains useful in accordance with a preferred aspect of the invention may carry the ability to produce a therapeutic molecule (or releases an agent such as a phagemid that carries the ability to generate therapeutic molecules) expressing plasmid or chromosomally integrated cassette that encodes and directs expression of one or more therapeutic molecules together with one or more protease inhibitors, as described herein. The protease inhibitors serve to prevent the destruction of the therapeutic molecule while within the tumor. If the cytotoxin and protease inhibitor diffuse outside of the tumor, they fall below the protease inhibitory concentration, and the cytotoxins are inactivated. Thus the protease inhibitor system both increases activity and provides tumor specificity.

The serovars of *S. enterica* that may be used as the attenuated bacterium of the live compositions described in accordance with various embodiments herein include, without limitation, *Salmonella enterica* serovar *Typhimurium* ("*S. typhimurium*"), *Salmonella montevideo, Salmonella enterica* serovar *Typhi* ("*S. typhi*"), *Salmonella enterica* serovar *Paratyphi* B ("*S. paratyphi* 13"), *Salmonella enterica* serovar *Paratyphi* C ("*S. paratyphi* C"), *Salmonella enterica* serovar *Hadar* ("*S. hadar*"), *Salmonella enterica* serovar *Enteriditis* ("*S. enteriditis*"), *Salmonella enterica* serovar *Kentucky* ("*S. kentucky*"), *Salmonella enterica* serovar *Infantis* ("*S. infantis*"), *Salmonella enterica* serovar *Pullorum* ("*S. pullorum*"), *Salmonella enterica* serovar *Gallinarum* ("*S. gallinarum*"), *Salmonella enterica* serovar *Muenchen* ("*S. muenchen*"), *Salmonella enterica* serovar *Anatum* ("*S. anatum*"), *Salmonella enterica* serovar *Dublin* ("*S. dublin*"), *Salmonella enterica* serovar *Derby* ("*S. derby*"), *Salmonella enterica* serovar *Choleraesuis* var. *kunzendorf* ("*S. cholerae kunzendorf*"), and *Salmonella enterica* serovar *minnesota* (*S. minnesota*). A preferred serotype for the treatment of bone marrow related diseases is *S. dublin.*

By way of example, live bacteria in accordance with aspects of the invention include known strains of *S. enterica* serovar *Typhimurium* (*S. typhimurium*) and *S. enterica* serovar *Typhi* (*S. typhi*) which are further modified as provided by various embodiments of the invention. Such Strains include Ty21a, CMV906, CMV908, CMV906-htr, CMV908-htr, Ty800, aroA-/serC-, holavax, M01ZH09, VNP20009. See also, U.S. Pat. No. 6,548,287, and EP 0,973,911, each of which expressly incorporated herein by reference. These strains contain defined mutations within specific serotypes of bacteria. The invention also includes the use of these same mutational combinations contained within alternate serotypes or strains in order to avoid immune reactions which may occur in subsequent administrations. In a preferred embodiment, *S. Typhimurium, S. montevideo*, and *S. typhi* which have non-overlapping O-antigen presentation (e.g., *S. typhimurium* is O—1, 4, 5, 12 and *S. typhi* is Vi, *S. montevideo* is O—6, 7) may be used. Thus, for example, *S. typhimurium* is a suitable serotype for a first injection and another serotype such as *S. typhi* or *S. montevideo* are used for a second injection and third injections. Likewise, the flagellar antigens are also selected for non-overlapping antigenicity between different injections. The flagellar antigen may be H1 or H2 or no flagellar antigen, which, when combined with the three different O-antigen serotypes, provides three completely different antigentic profiles. Methods for deriving heterologous O-antigens have been described by Favre et al., WO/1997/014782, and Roland WO/2000/004919, each of which is expressly incorporated herein by reference.

Novel strains are also encompassed that are, for example, attenuated in virulence by mutations in a variety of metabolic and structural genes. The invention therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is the Suwwan deletion (Murray et al., Journal of Bacteriology, 2004) or combinations with other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, pur, purA, purB, purl, purF, zwf, aroA, aroB, aroC, aroD, serC, gua, cadA, rfc, rjb, rfa, ompR, msbB and combinations thereof.

The invention also encompasses gram-positive bacteria. Preferred bacteria of the invention are group B *Streptococcus* including *S. agalaciae*, and *Listeria* species including *L. monocytogenes*. It is known to those skilled in the arts that minor variations in molecular biology techniques such as use of gram-positive origins of replication, gram-positive signal sequences gram-positive promoters and filamentous phage (e.g., phage B5; Chopin et al., 2002 J. Bacteriol. 184: 2030-2033) are required and substituted as needed.

The invention also provides, according to one embodiment, a process for preparing genetically stable therapeutic bacterial strains comprising genetically engineering the therapeutic genes of interest into a bacterially codon optimized expression sequence within a bacterial plasmid expression vector or chromosomal localization expression vector for any of the deleted genes or IS200 genes within the strain and further containing engineered restriction endonuclease sites such that the bacterially codon optimized expression gene contains subcomponents which are easily and rapidly exchangeable, and the bacterial strains so produced. Administration of the strain to the patient is therapeutic for the treatment of cancer.

The present invention provides, for example, and without limitation, live bacterial compositions that are genetically engineered to express one or more protease inhibitors combined with antitumor effector molecules or phagemids capable of delivering DNA and RNA therapeutics for the treatment of cancer.

4. DEFINITIONS

In order that the invention may be more fully understood, the following terms are defined.

As used herein, "attenuated", "attenuation", and similar terms refer to elimination or reduction of the natural virulence of a bacterium in a particular host organism, such as a mammal.

"Virulence" is the degree or ability of a pathogenic microorganism to produce disease in a host organism. A bacterium may be virulent for one species of host organism (e.g., a mouse) and not virulent for another species of host organism (e.g., a human). Hence, broadly, an "attenuated" bacterium or strain of bacteria is attenuated in virulence toward at least one species of host organism that is susceptible to infection and disease by a virulent form of the bacterium or strain of the bacterium.

As used herein, the term "genetic locus" is a broad term and comprises any designated site in the genome (the total genetic content of an organism) or in a particular nucleotide sequence of a chromosome or replicating nucleic acid molecule (e.g., a plasmid), including but not limited to a gene, nucleotide coding sequence (for a protein or RNA), operon, regulon, promoter, inducible promoters (including tetracycline, arabinose, (EP1,655,370 A1, expressly incorporated in its entirety herein), salicylic acid, hypoxic, tumor cell specific inducible promoters) regulatory site (including transcriptional terminator sites, ribosome binding sites, transcriptional inhibitor binding sites, transcriptional activator binding sites), origin of replication, intercistronic region, and portions therein. It is understood that all protein expression constructs require a stop signal. A genetic locus may be identified and characterized by any of a variety of in vivo and/or in vitro methods available in the art, including but not limited to, conjugation studies, crossover frequencies, transformation analysis, transfection analysis, restriction enzyme mapping protocols, nucleic acid hybridization analyses, polymerase chain reaction (PCR) protocols, nuclease protection assays, and direct nucleic acid sequence analysis The terms "oral", "enteral", "enterally", "orally", "non-parenteral", "non-parenterally", and the like, refer to administration of a compound or composition to an individual by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein to the lower intestinal tract of the alimentary canal.

The term "recombinant" is used to describe non-naturally altered or manipulated nucleic acids, cells transformed, electroporated, or transfected with exogenous nucleic acids, and polypeptides expressed non-naturally, e.g., through manipulation of isolated nucleic acids and transformation of cells. The term "recombinant" specifically encompasses nucleic acid molecules that have been constructed, at least in part, in vitro using genetic engineering techniques, and use of the term "recombinant" as an adjective to describe a molecule, construct, vector, cell, polypeptide, or polynucleotide specifically excludes naturally existing forms of such molecules, constructs, vectors, cells, polypeptides, or polynucleotides.

Cassette, or expression cassette is used to describe a nucleic acid sequence comprising (i) a nucleotide sequence encoding a promoter, (ii) a first unique restriction enzyme cleavage site located 5' of the nucleotide sequence encoding the promoter, and (iii) a second unique restriction enzyme cleavage site located 3' of the nucleotide sequence encoding the promoter. The cassette may also contain a multiple cloning site (MCS) and transcriptional terminator within the 5' and 3' restriction endonuclease cleavage sites. The cassette may also contain cloned genes of interest.

As used herein, the term "*salmonella*" (plural, "salmonellae") and "*Salmonella*" refers to a bacterium that is a serovar of *Salmonella enterica*. A number of serovars of *S. enterica* are known. Particularly preferred *salmonella* bacteria useful in the invention are attenuated strains of *Salmonella enterica* serovar *Typhimurium* ("*S. typhimurium*") and serovar *Typhi* ("*S. typhi*") as described herein.

As used herein, the terms "strain" and "isolate" are synonymous and refer to a particular isolated bacterium and its genetically identical progeny. Actual examples of particular strains of bacteria developed or isolated by human effort are indicated herein by specific letter and numerical designations (e.g. strains Ty21a, CMV906, CMV908, CMV906-htr, CMV908-htr, Ty800, holavax, M01ZH09, VNP20009).

The definitions of other terms used herein are those understood and used by persons skilled in the art and/or will be evident to persons skilled in the art from usage in the text.

5. BRIEF DESCRIPTION OF THE DRAWINGS

6. DETAILED DESCRIPTION OF THE INVENTION

The present invention provides, according to various embodiments, improved live attenuated therapeutic bacterial strains that express one or more therapeutic molecules together with one or more protease inhibitor polypeptides that inhibit local proteases that could deactivate the therapeutic molecules. In particular, one aspect of the invention relates to live attenuated tumor-targeted bacterial strains that may include *Salmonella* vectoring novel chimeric anti-tumor toxins to an individual to elicit a therapeutic response against cancer. The types of cancer may generally include solid tumors, leukemia, lymphoma and multiple myeloma. In addition, certain of the therapeutic molecules have co-transmission requirements that are genetically unlinked to the therapeutic molecule(s), limiting certain forms of genetic exchange. Another aspect of the invention relates to live attenuated tumor-targeted bacterial strains that may include *Salmonella* vectoring filamentous phage that encode anti-tumor DNA and RNA molecules to an individual to elicit a therapeutic response against cancer including cancer stem cells. The filamentous phage may also be targeted to tumor matrix cells, and immune cells. Another aspect of the invention relates to reducing or eliminating the bacteria's ability to undergo conjugation, further limiting incoming and outgoing exchange of genetic material.

For reasons of clarity, the detailed description is divided into the following subsections: protease sensitivity; protease inhibitors; targeting ligands; chimeric bacterial toxins; co-expression of protease inhibitors with bacterial toxins, segregation of required colicin cofactors; limiting bacterial conjugation; phage/phagemid producing gram negative bacteria encoding therapeutic DNA and RNA molecules.

6.1. Protease Sensitivity.

The therapeutic proteins of the invention are sensitive to proteases (in contrast pro-aerolysin or urokinase chimeric toxins that are activated by proteases). Protease digestion sites may be added to the therapeutic agent to enhance protease sensitivity. Preferred proteases for conferring greater sensitivity are those that are under-expressed in tumors and over-expressed in normal tissues. Other proteases for which sensitivity sights may be added include tissue plasminogen activator, activated protein C, factor Xa, granzyme (A, B, M), cathepsins, thrombin, plasmin, urokinase, matrix metaloproteaes, prostate specific antigen (PSA) and kallikrein 2.

6.2.1 Protease Inhibitors

Protease inhibitors of the invention are preferably based on known polypeptide inhibitors. The inhibitors include both synthetic peptides and naturally occurring, endogenous peptides.

Figure 2:
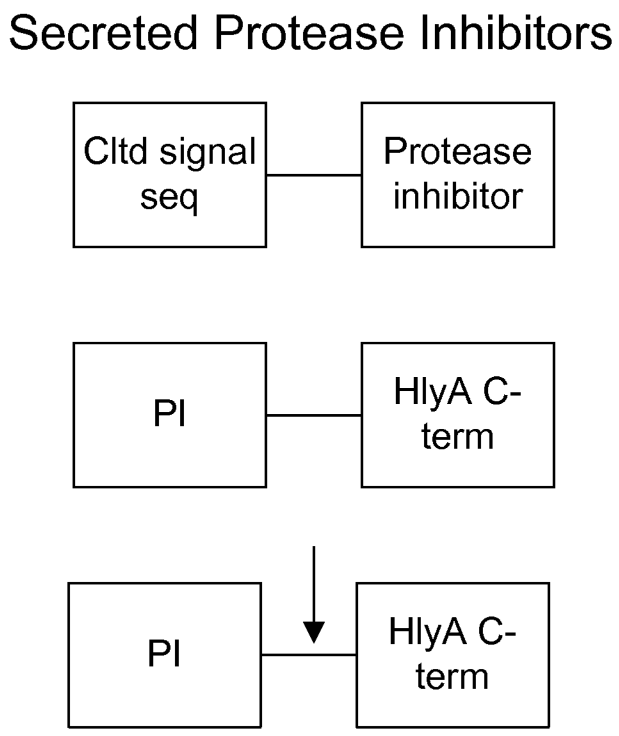
FIG. 2 shows secreted protease inhibitors.

To result in the desired activity, the peptides should be secreted outside of the bacteria. Accordingly, the peptides are modified by fusing them to secretion signals. The secretion signals may be either N-terminal (derived from ompA, ompF, M13pIII, cldt) or C-terminal (last 60 amino acids of the *E. coli* HlyA hemolysin, together with the required HlyBD supplied in trans and endogenous tolC) as shown in FIG. 2. The N-terminal signal sequences are well known and characterized by the presence of a protease cleavage site for an endogenous bacterial protease. Thus, N-terminal signal sequences provide free protease inhibitors, free from the signal sequence. The C-terminal signal sequence may be further engineered to have a protease cleavage site in between the protease inhibitory peptide and the signal sequence. The cleavage site may be for the same protease that the peptide inactivates. Thus, the protease activates its own inhibitor. The protease cleavage site may also be for a protease other than for the protease inhibitor, thus deactivating another protease. Proteases upregulated within tumors for which protease cleavage sites may be engineered include: tissue plasminogen activator, activated protein C, factor Xa, granzyme (A, B, M), cathepsin, thrombin, plasmin, urokinase, matrix metaloproteaes, prostate specific antigen (PSA) and kallikrein 2.

Suitable protease inhibitors, include, but are not limited to, those listed below.

| | |
|---|---|
| Furin inhibitors: | |
| PAAATVTKKVAKSPKKAKAAKPKKAAKSAAK AVKPK | SEQ ID NO: 1 |
| TKKVAKRPRAKRAA | SEQ ID NO: 2 |
| TKKVAKRPRAKRDL | SEQ ID NO: 3 |
| GKRPRAKRA | SEQ ID NO: 4 |
| CKRPRAKRDL | SEQ ID NO: 5 |
| CVAKRPRAKRDL | SEQ ID NO: 6 |
| CKKVAKRPRAKRDL | SEQ ID NO: 7 |
| RRRRRR L6R (hexa-L-arginine) | SEQ ID NO: 8 |
| Inhibitors of kallikrein 2: | |
| SRFKVWWAAG | SEQ ID NO: 9 |
| AARRPFPAPS | SEQ ID NO: 10 |
| PARRPFPVTA | SEQ ID NO: 11 |
| Tissue protease inhibitor | |
| DSLGREAKCYNELNGCTKIYDPVCGTDGNTYPN ECVLCFENRKRQTSILIQKSGPC (serine protease inhibitor, Kazal type 1, mature) | SEQ ID NO: 12 |

Other suitable protease inhibitors are described in Rawlings et al., 2010, MEROPS: The Peptidase Database, Nucleic Acids Res. 2010 (Database issue):D227-33, the entirety of which is expressly incorporated herein by reference. Suitable protease inhibitors also encompass functional fragments, respective homologs, and respective analogs, of the sequences described in Rawlings et al., and also other known peptide protease inhibitors including those described in Brinkmann et al, 1991 Eur J. Biochem 202: 95-99; Dunn et al., 1983 Biochem J 209: 355-362; Feng et al., (WO 2004/076484) PEPTIDE INHIBITORS OF THROMBIN AS POTENT ANTICOAGULANTS); and Markowska et al., 2008, Effect of tripeptides on the amindolytic activities of urokinase, thrombin, plasmin and trypsin. Int. J. Peptide Research and Therapeutics 14: 215-218, each of which is expressly incorporated herein by reference.

Targeting Ligands

Targeting ligands are used to both confer specificity to chimeric proteins or phages, but also to direct internalization. The ligands of various aspects of the present invention are peptides that can be expressed as fusions with other bacterially-expressed proteins. The peptides may be further modified, as for gastrin and bombesin, in being amidated by a peptidylglycine-alpha-amidating monoxygenase or C-terminal amidating enzyme, which is co-expressed in the bacteria that use these peptides using standard molecular genetic techniques.

TABLE 2

| Examples of targeting peptides | | |
|---|---|---|
| Peptide sequence or ligand name | Receptor or Target | Reference |
| TGF-alpha | EGFR | |
| SYAVALSCQCALCRR<br>CG-beta<br>SEQ ID NO: 13 | | Rivero-Muller et al., Moleclar and Cellular Endocrinology 2007: 17-25<br>Morbeck et al., 1993 |
| AVALSCQCALCRR<br>CG-beta (ala truncation)<br>SEQ ID NO: 14 | | Jia et al., Journal of Pharmacy and Pharmacology 2008; 60: 1441-1448 |
| Leuteinizing hormone-releasing hormone (LHRH)<br>pyroGlu-His-Trp-Ser-Tyr-Gly-Leu-Arg-Pro-Gly CONH2<br>SEQ ID NO: 15 | LHRH receptor | |
| IL2 | IL2R | Frankel et al. 2000, Clinical Cancer Research 6: 326-334. |
| Tf | TfR | Frankel et al. 2000, Clinical Cancer Research 6: 326-334. |
| IL4 | IL4R | Frankel et al. 2000, Clinical Cancer Research 6: 326-334. |
| GM-CSF | GM-CSFR | Frankel et al. 2000, Clinical Cancer Research 6: 326-334. |
| | CD-19 | |
| Bombesin | Gastrin releasing peptide receptor | Dyba M., Tarasova N. I., Michejda C. J. Small molecule toxins targeting tumor receptors. Curr. Pharm. Des., 2004, 10 (19), 2311-2334. |
| Gastrin releasing peptide | Gastrin releasing peptide receptor | |
| somatostatin octapeptide RC-121 (D-Phe-Cys-Tyr-D-Trp-Lys-Val-Cys-Thr-NH2<br>SEQ ID NO: 16 | | |
| somatostatin | | |
| Vasoactive intestinal peptide (VIP Neurtensin) | | |
| Parathyroid hormone-related protein PTHrP N-terminal 36 resides also has nuclear targeting | Parathyroid hormone receptor G-protein coupled receptor | |
| KLAKLAKKLALKLA<br>SEQ ID NO: 17 | Proapoptotic peptide | |
| | Endoglin (CD105) | |
| | KCNK9 | |
| | Mesothelin | |
| | EGFR | |
| | Mucin | |
| Heat stable enterotoxin (ST)<br>NSSNYCCELCCNPACTGCY<br>SEQ ID NO: 18 | Guanylyl cyclase C | |
| Mature peptide<br>1 VLSFSPFAQD AKPVESSKEK ITLESKKCNI AKKSNKSDPE SMNSSNYCCE LCCNPACTGC 61 Y<br>SEQ ID NO: 19 | Heat stable enterotoxin unprocessed | |
| CM-CSF | AML | |
| | Alfa(V)Beta(3) integrin | |
| | STEAP-1 (six transmembrane antigen of the prostate) | |
| CDCRGDCFC<br>SEQ ID NO: 20 | RGD 4C: active peptide targeting the $_v\beta_3$ integrin) | Line et al. 46 (9): 1552. (2005) Journal of Nuclear Medicine |
| LGPQGPPHLVADPSKKQGP WLEEEEEAYGWMDF<br>SEQ ID NO: 59<br>(gastrin-34) or big gastrin | bind to the gastrin receptor, also known in the art as the cholecystokinin B (CCKB) receptor | |
| MGWMDF<br>SEQ ID NO: 21 | | |

TABLE 2-continued

| Examples of targeting peptides | | |
|---|---|---|
| Peptide sequence or ligand name | Receptor or Target | Reference |
| N-terminal truncation of gastrin VPLPAGGGTVLTKM YPRGNHWAVGHLM SEQ ID NO: 22 | Gastrin releasing peptide | |
| CAYHLRRC SEQ ID NO: 23 | AML | Nishimra et al., 2008. J Biol Chem 283: 11752-11762 |
| CAY (cys-ala-tyr) SEQ ID NO: 24 | Lymph node homing | Nishimra et al., 2008. J Biol Chem 283: 11752-11762 |
| RLRR (arg-le-arg-arg) SEQ ID NO: 25 | Cell penetrating | Nishimra et al., 2008. J Biol Chem 283: 11752-11762 |
| VRPMPLQ SEQ ID NO: 26 | Colonic dysplasia | Hsiung et al, Nature Medicine 14: 454-458 |
| HVGGSSV SEQ ID NO: 27 | 2622 Radiation-Induced Expression of Tax-Interacting Protein 1 (TIP-1) in Tumor Vasculature Binds irradiated tumors ie, ones responding to therapy | International Journal of Radiation Oncology Biology Physics, Volume 66, Issue 3, Pages S555-S556 H. Wang, A. Fu, Z. Han, D. Hallahan |
| CGFECVRQCPERC SEQ ID NO: 28 | Lung vasculature - MOSE Binds membrane dipeptidase (MDP) | Mori 2004 Current Pharmaceutical Design 10: 2335-2343 |
| SMSIARL SEQ ID NO: 29 | MURINE PROSTATE VASCULATURE | Mori 2004 Current Pharmaceutical Design 10: 2335-2343 |
| VSFLEYR SEQ ID NO: 30 | MURINE PROSTATE VASCULATURE | Mori 2004 Current Pharmaceutical Design 10: 2335-2343 |
| Fragment 3 of the high mobility group (HMG)N2 CKDEPQRRSARLSAKPAPP KPEPKPKKAPAKK SEQ ID NO: 31 | | |
| H-VEPNCDIHVMW EWECFERL-NH2 SEQ ID NO: 32 | VEGF BINDING PEPTIDE | (WO/2006/116545) SPATIAL CONTROL OF SIGNAL TRANSDUCTION |
| RLLDTNRPLLPY SEQ ID NO: 33 | L-PEPTIDE Nasopharyngeal Phage derived - caused internalization of phage | Let al., 2004. Cancer Research 64: 8002-8008. |
| RGDLATL truncated RGDLATLRQLAQEDGVVGVR SEQ ID NO: 34 | Alfa(v) beta (6) integrin | Shunzi et al. (Kathyll C Brown |

6.3 Small Lytic Peptides

Small lytic peptides (less than 50 amino acids) are used to construct chimeric proteins for more than one purpose. The chimeric proteins containing lytic peptides may be directly cytotoxic for the cancer cells, and/or other cells of the tumor including the tumor matrix cells and immune cells which may diminish the effects of the bacteria by eliminating them. In order to be cytotoxic they must be secreted (FIGS. 4A to 4D and 5A to 5D) and may be provided with cell specificity by the addition of a targeting ligand. Furthermore, the lytic peptides are useful in chimeric proteins for affecting release from the endosome. Small lytic peptides have been used in the experimental treatment of cancer. However, it is evident that most, if not all, of the commonly used antitumor small lytic peptides have strong antibacterial activity, and thus are not compatible with delivery by a bacterium (see Table 1 of Leschner and Hansel, 2004 Current Pharmaceutical Design 10: 2299-2310, expressly incorporated herein by reference). Small lytic peptides useful in the invention are those derived from *Staphylococcus aureus, S. epidermidis* and related species, including the phenol-soluble modulin (PSM) peptides and delta-lysin (Wang et al., 2007 Nature Medicine 13: 1510-1514, expressly incorporated herein by reference). The selection of the lytic peptide depends upon the primary purpose of the construct, which may be used in combination with other constructs providing other anticancer features. That is, the therapies provided in accordance with aspects of the present invention need not be provided in isolation, and the bacteria may be engineered to provide additional therapies or advantageous attributes. Constructs designed to be directly cytotoxic to cells employ the more cytoxic peptides, particularly PSM-alpha-3. Constructs which are designed to use the lytic peptide to affect escape from the endosome use the peptides with the lower level of cytotoxicity, such as PSM-alpha-1, PSM-alpha-2 or delta-lysin.

TABLE 3

| Membrane lytic peptides useful in the invention | |
|---|---|
| Peptide and source | Peptide Sequence |
| Processed << short >> active delta lysin *S aureus* | MAQDIISTISDLVKWIIDTVNKFTKK SEQ ID NO: 35 |
| Delta lysin processed *S epidermitidis* | MMAADIISTIGDLVKWIIDTVNKFKK SEQ ID NO: 36 |
| Delta lysin from CA-MRSA | MAQDIISTISDLVKWIIDTVNKFTKK SEQ ID NO: 37 |
| PSM-alpha-1 | MGIIAGIIKVIKSLIEQFTGK SEQ ID NO: 38 |
| PSM-alpha-2 | MGIIAGIIKFIKGLIEKFTGK SEQ ID NO: 39 |
| PSM-alpha-3 | MEFVAKLFKFFKDLLGKFLGNN SEQ ID NO: 40 |
| PSM-alpha-4 | MAIVGTIIKIIKAIIDIFAK SEQ ID NO: 41 |
| PSM-beta-1 | MEGLFNAIKDTVTAAINNDGAKLGTSIVS IVENGVGLLGKLFGF SEQ ID NO: 42 |
| PSM-beta-2 | MTGLAEAIANTVQAAQQHDSVKLGTSIV DIVANGVGLLGKLFGF SEQ ID NO: 43 |

6.4 Chimeric Bacterial Toxins

Chimeric toxins are used to adapt secreted bacterial proteins to provide therapeutic molecules that are effective in treating tumor cells, tumor stem cells as well as immune infiltrating cells. Targeting to a particular cell type uses the appropriate ligand from the Table 2 above or from other known sources.

6.4.1 Chimeric colicins. Colicins lack tumor cell targeting. In the present invention, the colicin targeting and translocation domains are replaced with an M13pIII-derived signal sequence and truncated membrane anchor together with a targeting ligand. A lytic peptide may also be added. Examples of the unique organization for chimeric colE3, colE7 and col-Ia are shown in FIGS. 3A to 3F.

6.4.2 Chimeric cytolethal distending toxin. Cytolethal distending toxin (cldt) is a three component toxin of *E. coli, Citrobacter, Helicobacter* and other genera. Cldt is an endonuclease toxin and has a nuclear localization signal on the B subunit. Chimeric toxins are provided that utilize fusion to apoptin, a canary virus protein that has a tumor-specific nuclear localization signal, a normal cell nuclear export signal (FIGS. 6A to 6D). The cytolethal distending toxin B and chimeric cltdB may be expressed as a polycistronic construct consisting of cldtABC. The cytolethal distending toxin B and chimeric cltdB may be expressed as a polycistronic construct consisting containing the typhoid pertussis-like toxin (plt) AB genes.

6.4.3 RTX toxins and hybrid operons. *E. coli* HlyA(s) operon hlyCABD (+TolC), *Actinobacillus actinomycetemcomitans* leukotoxin ltxCABD, and a hybrid CABD operon are shown in FIGS. 7A to 7D. The ltxA may be generated as a chimera wherein it contains the C-terminal 60 amino acids of the *E. coli* HlyA. The ltx genes and chimeras may be expressed together with prtF and/or cyaE.

6.4.4 Saporin and ricin chimeras. Saporin and ricin can be replaced for the active portion of the colicin chimeras (FIGS. 3A to 3F). It can also be generated as a targeting peptide, saporin, HlyA C-terminus.

6.4.5 Cytotoxic necrotic factor (cnf) and *Bordetella* dermonecrotic factor (dnf) chimeras. Cnf and dnf can be expressed as chimeras, where the N-terminal binding domain (amino acids 53 to 190 of cnf) is replaced with a tumor cell binding ligand, such as TGF-alpha.

6.4.6 Shiga toxin (ST) and shiga-like toxin (SLT) chimeras. ST and SLT chimeras are generated wherein the GB3-binding domain is replaced with a tumor cell binding ligand, such as TGF-alpha.

6.4.7 Subtilase toxin chimeras. Subtilase chimeras are generated by replacing the binding domain with a tumor cell binding ligand, such as TGF-alpha.

6.5 Limiting Bacterial Conjugation.

Figure 8:
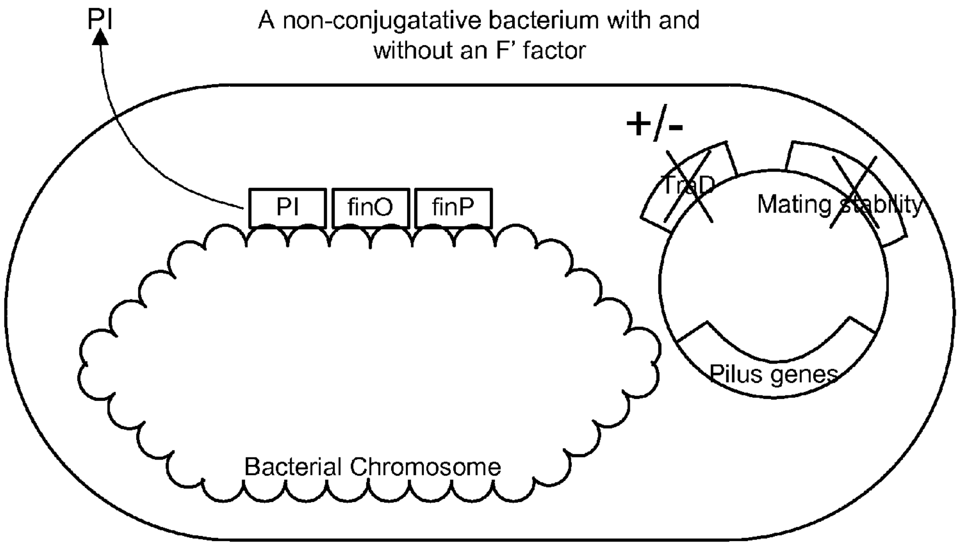
FIG. 8 shows a non-conjugative bacterium with and without the F' factor.

The fertility inhibition complex (finO and finP), are cloned onto the chromosome using standard genetic techniques such that strains either with or without the pilus resistant to mating with F' bacteria (FIG. 8). Other known inhibitory factors may also be used.

The F' pilus factors in a *Salmonella* strain needed for phage to be able to infect the cell are provided by the F' plasmid using standard mating techniques from an F' *E. coli*. The F' factor provides other functions such as traD and the mating stabilization which are deleted using standard techniques.

6.6 Co-Expression of Protease Inhibitors with Bacterial Toxins and Determination of Synergy Each of the bacterial toxins listed herein may be improved in its therapeutic activity by co-expression with a protease inhibitor. Inhibitors are expressed as secreted proteins as described above. The effect of the protease inhibitor on in vitro cytotoxicity is determined using standard cell culture techniques and cytotoxicity assays such as MTT known to those skilled in the arts. The contribution of the protein cytotoxin and protease inhibitors is determined individually and in combination. Synergy may determined using the median effect analysis (Chou and Talaly 1981 Eur. J. Biochem. 115: 207-216) or other standard methods. The assay may be further modified to include addition of a specific protease. The assay may also be used to determine synergy, additivity or antagonism of two or more bacterial cytotoxins. The assay may also be used to determine synergy, additivity or antagonism a bacterial cytotoxin together with a conventional small molecule cytotoxin (e.g., Cisplatin, doxorubicin, irinotecan, Paclitaxel or vincristine), targeted therapeutic (e.g., imatinib, irissa, cetuximab), proteosome inhibitor (bortezomib), mTOR inhibitor. In vivo studies may also be performed with antiangiogenic inhibitors such as Avastin, combretastatin, or thalidomide. In vivo studies with reticuloendothelial system (RES) blocker such as chlodronate which have the potential to improve the circulation time of the bacteria, vascular permeability inducing agents such as bradykinin, hyperthermia or carbogen which have the potential to improve the permeability of the tumor enhancing entry of the bacteria, or aldose reductase inhibitors.

6.7 Segregation of Required Colicin Toxin Cofactors.

Figure 9:
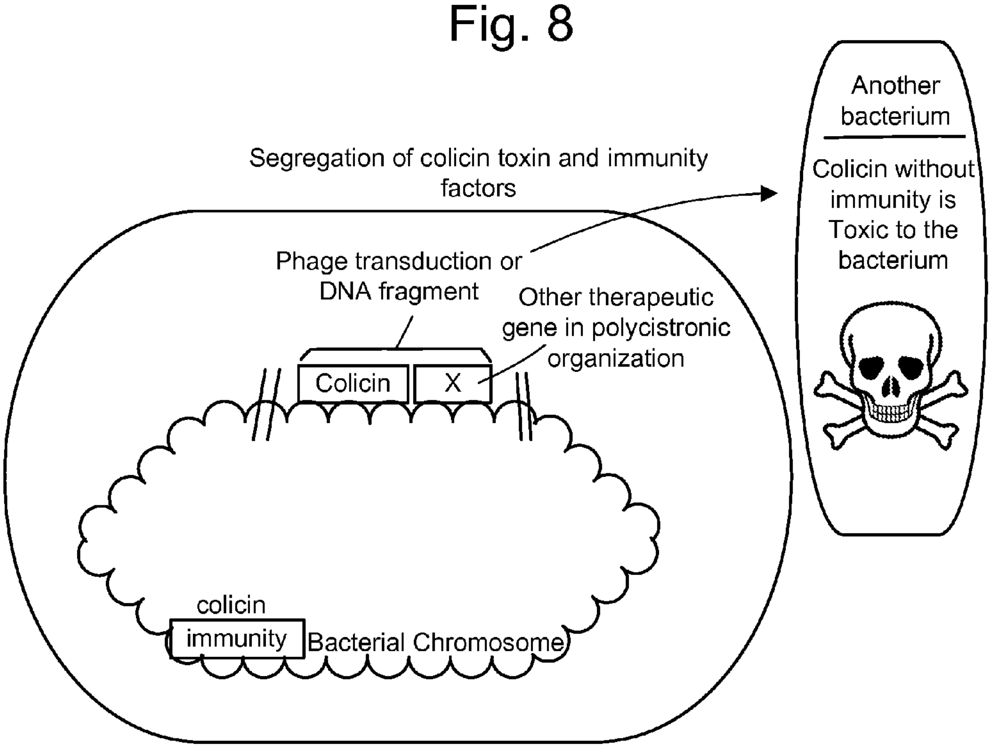
FIG. 9 shows segregation of required colicin toxin and immunity factors.

The chimeric colicin toxins have active colicin components that require their respective immunity proteins, which are usually genetically linked. By unlinking the two genes and separating them on the chromosome, a single fragment or phage transduction is highly unlikely to contain both elements. Without both elements, the toxin portion cannot be carried and will kill most bacteria. Any additional genes such as other chimeric therapeutic molecules genetically linked to the colicin will also be inhibited from being transferred to other bacteria (FIG. 9)

Figure 10:
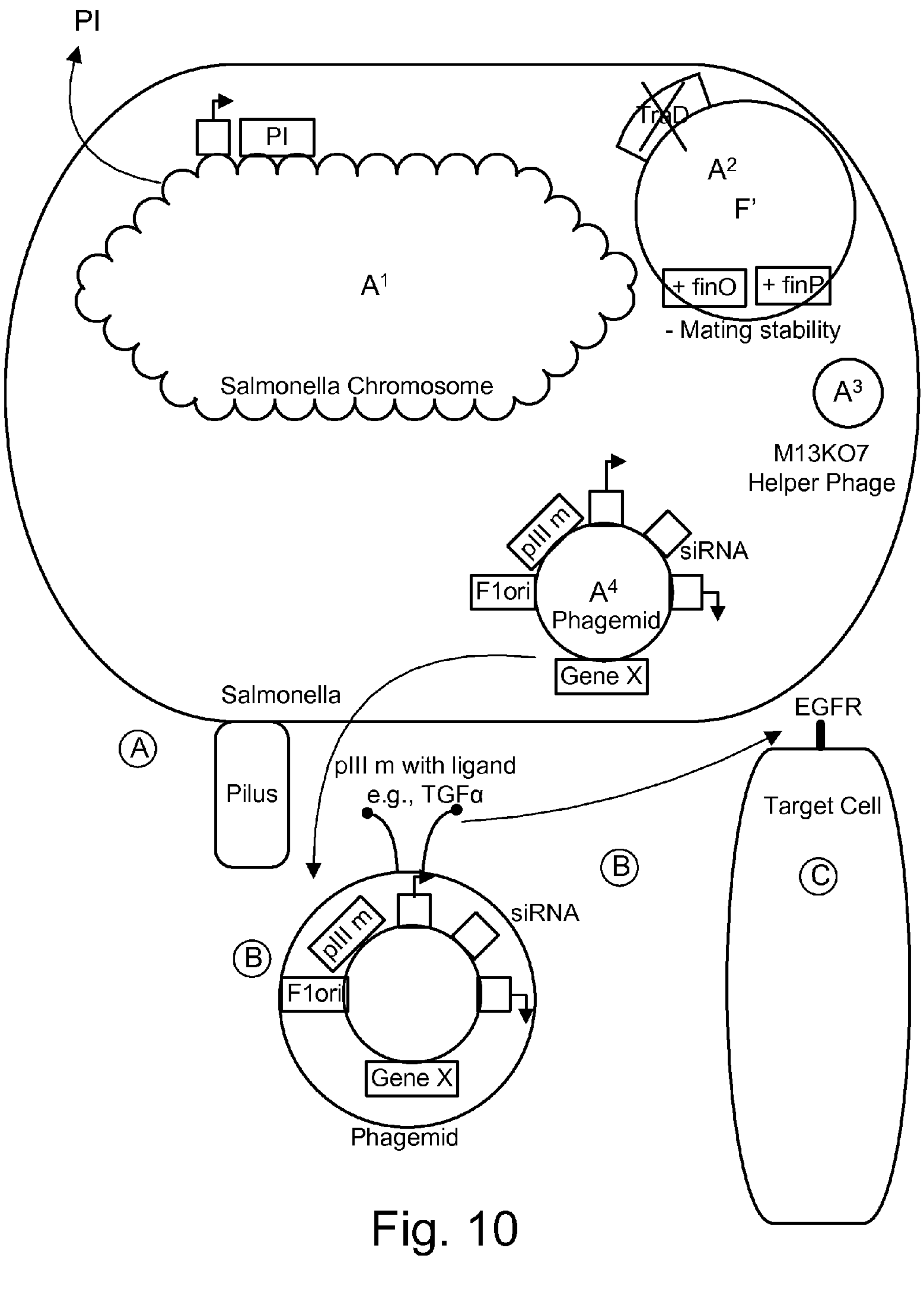
FIG. 10 shows a non-conjugative bacterium capable of releasing phage/phagemids carrying expression constructs for DNA and RNA therapeutics.

6.8 Phage/Phagemid Producing Gram-Negative Bacteria Encoding Therapeutic DNA and RNA Molecules (FIG. 10).

The F' pilus containing bacterium (FIG. 8) with deletions relating to conjugation and is expressing a protease inhibitor (PI) that is secreted into the medium are first infected with a helper phage, such as M13K07 which is able to use the pilus for entry. The helper phage may be further modified to lack an antibiotic resistance maker such as the kanamycin marker. Next, a phagemid (hybrid plasmid:phage which has the F' origin such as one derived from pEFGP-N1) containing a pIII fusion with a targeting peptide, and optionally, a lytic peptide fusion to pVIII, and one or more therapeutic genes which could be a DNA encoding a functional p53 protein, or a gene encoding small interfering RNA molecules (siRNA) or microRNA (miRNA) molecules or other RNA interfering (RNAi) molecules or constructs that mediate RNA interference for an oncogene such as KRAS is transfected into the bacterial cell. The phagemid may also encode the T7 polymerase, and the effector gene such as one encoding the siRNA and/or miRNA and/or RNAi construct may be driven by the T7 promoter. The phage may also contain self-complementary sequences that induce the formation of double-stranded filamentous phage. Pieto and Sanchez 2007 Biochmica et Biophysica Acta 1770:1081-1084 regarding self-complementary sequences that induce the formation of double-stranded filamentous phage), expressly herein incorporated by reference. Now, the phagemid, in the presence of the helper phage, is replicated as single stranded DNA and packaged into a filamentous phagemid that is secreted outside of the bacterium. Because the phagmid contains pIII fusions with a targeting ligand, such as TGF-alpha, the phage are able to bind to the target cell, enter, release their DNA which then is transcribed into the respective therapeutic molecules and results in an antitumor effect. When administered to a patient with a tumor for which the appropriate receptor has been selected, the bacterium carrying the phagemids results in a therapeutic effect. The effect may be further enhanced by co-administration of camptothecin as described by Burg et al. See, Burg et al., "Enhanced Phagemid Particle Gene Transfer in Camptothecin-treated Carcinoma Cells", Cancer Research 62: 977-981 (2002), expressly incorporated herein by reference.

7. FIGURE LEGENDS

Figure 1A:
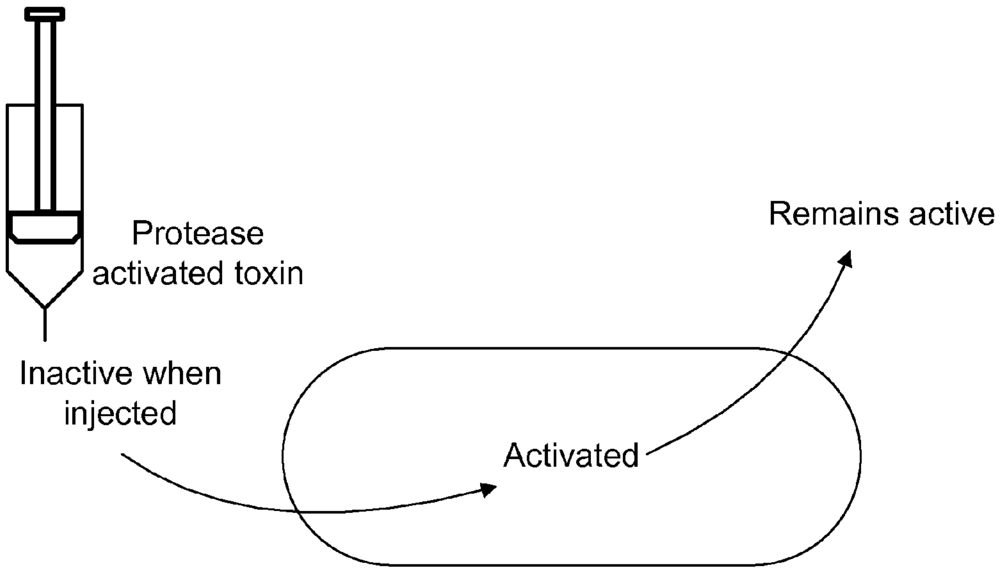
FIGS. 1A and 1B show a comparison of tumor-protease activated toxin with tumor protease inhibitor (FIG. 1A) and protease sensitive toxin expression system (FIG. 1B).
Figure 1B:
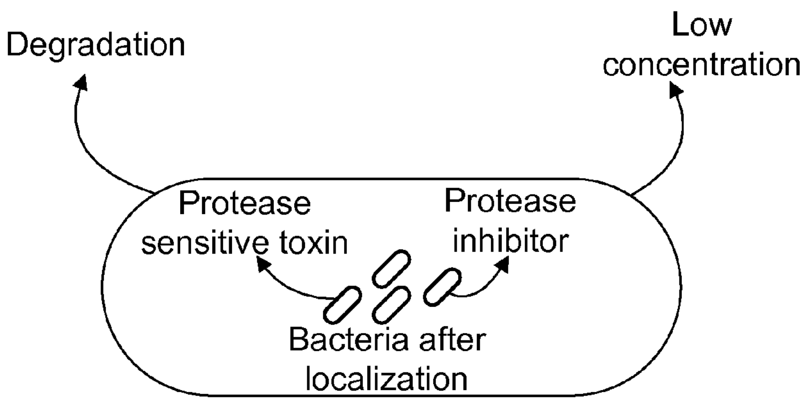

FIGS. 1A and 1B. Comparison of tumor-protease activated toxin with tumor protease inhibitor and protease sensitive toxin expression. FIG. 1A. Intravenously injected tumor protease activated toxin remains active if it diffuses out of the tumor. FIG. 1B. Intratumoral bacteria co-expressing a protease inhibitor and a protease sensitive toxin achieve high intratumoral activity and degredation following diffusion out of the tumor. The co-expression system results in high intratumoral activity, achieving a therapeutic benefit with low toxicity.

FIG. 2. Secreted protease inhibitors. A) An N-terminal signal sequence from a cytolethal distending toxin gene followed by a protease inhibitor (PI). B) A PI followed by the hlyA C-terminal signal sequence. C) A PI followed by the hlyA C-terminal signal sequence with a protease cleavage site (downward arrow).

Figures 3A, 3B, 3C, 3D, 3E, 3F:
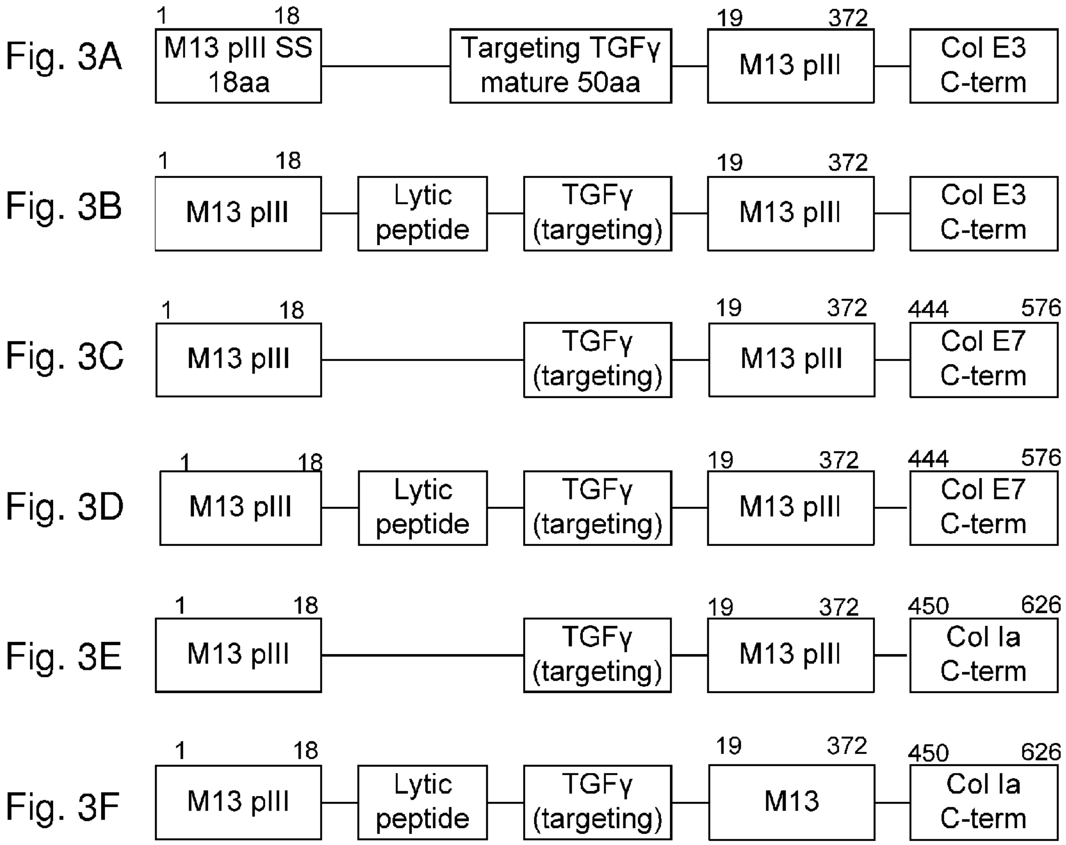
FIGS. 3A to 3F show chimeric colicins.

FIGS. 3A to 3F show chimeric colicins. FIG. 3A shows an M13 pIII signal sequence with amino acids 1 to 18 followed by a targeting peptide (TGF-alpha), a membrane anchor truncated M13 pIII amino acids 19 to 372 and the C-terminus of ColE3 (ribonuclease). The colicin is secreted, the signal sequence cleaved and the targeting peptide targets the EGFR-expressing cancer cell. FIG. 3B shows a lytic peptide is added between the signal sequence and the targeting peptide. Following cleavage of the signal sequence, the targeting peptide localizes to the EFGF-expressing cancer cell and the lytic peptide assists in its release from the endosome. FIG. 3C shows a ColE7 (DNAase) chimera. FIG. 3D shows a ColE7 chimera with a lytic peptide. FIG. 3E shows a Col-Ia (membrane channel forming peptide) chimera. FIG. 3F shows a Col-Ia chimera with a lytic peptide.

Figure 4A:
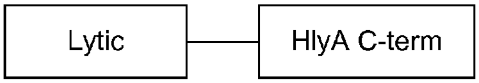
FIGS. 4A to 4D show lytic peptide chimeras.
Figure 4B:
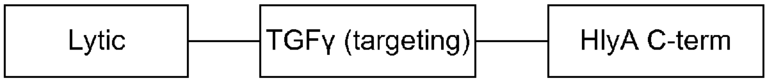
Figure 4C:
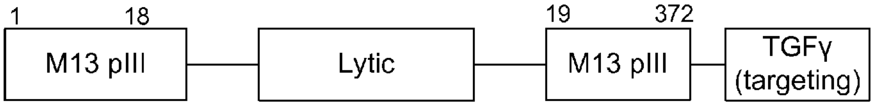
Figure 4D:

FIGS. 4A to 4D show lytic peptide chimeras. FIG. 4A shows a lytic peptide followed by the hlyA signal sequence. FIG. 4B shows a lytic peptide, targeting peptide (TGF-alpha), hlyA signal peptide chimera. FIG. 4C shows the M13 pIII signal sequence followed by a lytic peptide, the membrane anchor truncated M13 pIII amino acids 19 to 372 and a targeting peptide (TGF-alpha). FIG. 4D shows the M13 pIII signal sequence followed by a lytic peptide and a targeting peptide (TGF-alpha).

Figure 5A:
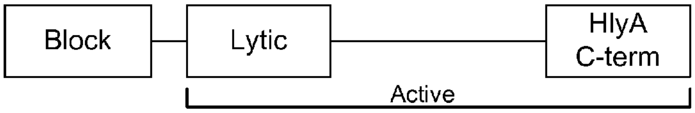
FIGS. 5A to 5D show protease activated lytic peptide chimera prodrugs.
Figure 5B:
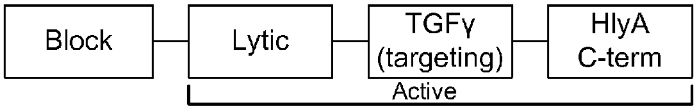
Figure 5C:
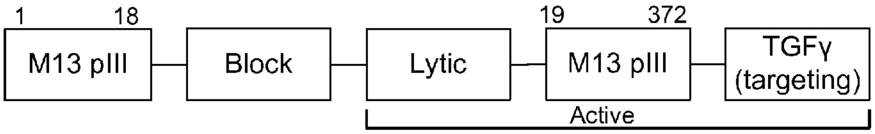
Figure 5D:
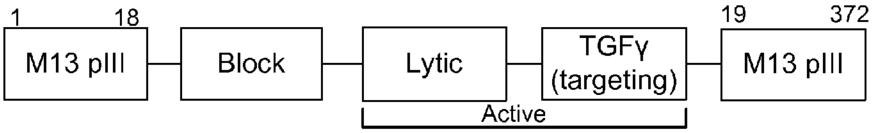

FIGS. 5A to 5D show protease activated lytic peptide chimera prodrugs. FIG. 5A shows a blocking peptide followed by a tumor protease cleavage site, a lytic peptide followed by the hlyA signal sequence. The bracket underneath shows the active portion of the chimera following proteolytic cleavage. FIG. 5B shows a blocking peptide followed by a tumor protease cleavage site, a lytic peptide, targeting peptide (TGF-alpha) followed by a second tumor protease cleavage site and the hlyA signal peptide. FIG. 5C shows the M13 pIII signal sequence followed by a blocking peptide with a tumor protease cleavage site, a lytic peptide, the membrane anchor truncated M13 pIII amino acids 19 to 372 and a targeting peptide (TGF-alpha). FIG. 5D shows the M13 pIII signal sequence followed by a blocking peptide with a tumor protease cleavage site, a lytic peptide, a targeting peptide (TGF-alpha) with a tumor protease cleavage site and the membrane anchor truncated M13 pIII amino acids 19 to 372.

Figure 6A:
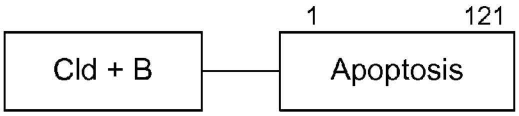
FIGS. 6A to 6D show cytolethal distending toxin subunit B (cldtB) chimeras.
Figure 6B:
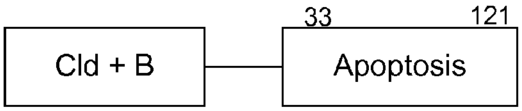
Figure 6C:
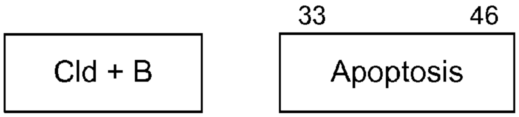
Figure 6D:
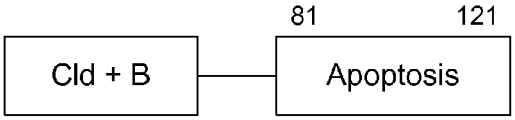

FIGS. 6A to 6D show cytolethal distending toxin subunit B (cldtB) chimeras. It is understood that full functionality requires cltdA and cltdC. FIG. 6A shows CldtB followed by apoptin 1 to 121. FIG. 6B shows CldtB followed by apoptin 33 to 121. FIG. 6C shows CldtB followed by apoptin 33-46. FIG. 6D shows CldtB followed by apoptin 81-121.

FIGS. 7A to 7D show repeat in toxin (RTX) family members and hybrid operons.

Figure 7A:
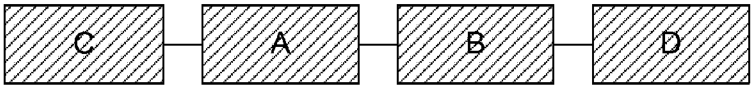
FIGS. 7A to 7D show repeat in toxin (RTX) family members and hybrid operons.
Figure 7B:
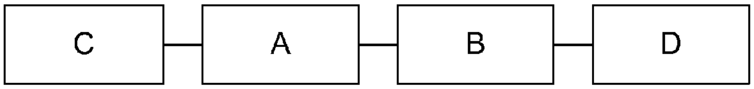

FIG. 7A shows HlyCABD from *E. coli*. FIG. 7B shows LtxCABD from *Actinobacillus*.

Figure 7C:
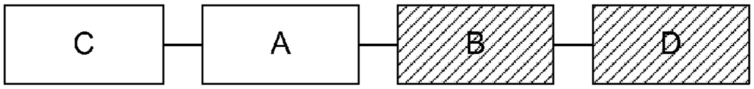
Figure 7D:
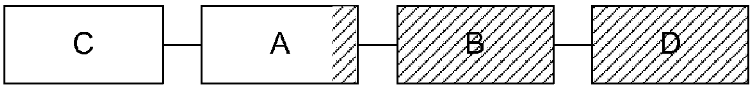

FIG. 7C shows a hybrid CABD of *E. coli* (HlyBD) and *Actinobacillus* (HlyCA). FIG. 7D shows a hybid ltxCA with *E. coli* BD where the ltxA contains the C-terminal 60 amino acids of HlyA.

FIG. 8. A non-conjugative bacterium with and without the F' factor. The bacterial chromosome contains a secreted protease inhibitor construct (PI) that results in a secreted protease inhibitor. The chromosome also contains the FinO and FinP genes in order to inhibit conjugation. When present, the F' factor containing the pilus genes with deletions relating to conjugation in traD and the mating stabilization (MS) results in a pilus expressed by the bacterium.

FIG. 9. Segregation of colicin toxin and required immunity factor(s). The bacterial chromosome has a colicin immunity protein integrated into a neutral sight (e.g., attenuating mutation or IS200 element). The colicin, or colicin hybrid is not linked to the immunity protein, but is distal to it. Other therapeutic molecules may be in the same proximity, such as in a polycistronic organization. Based on this organization, a random DNA fragment, or a portion of the genome packaged by a transducing phage, could not contain the immunity protein. If such a fragment were transferred to another bacterium, expression of the colicin without the immunity protein would kill the bacterium.

FIG. 10. A.) A1. The bacterial chromosome contains a secreted protease inhibitor construct (PI) that results in a secreted protease inhibitor. A2. The F' factor containing the pilus genes with deletions relating to conjugation in traD and the mating stabilization results in a pilus expressed by the bacterium. The FinO and FinP genes are inserted onto the F' in order to further inhibit conjugation. A3. A helper phage such as M13K07 provides phage functions for replication and packaging. A4. A phagemid (hybrid plasmid:phage which has the F' origin) containing a pIII fusion with a targeting peptide, and optionally, a lytic peptide fusion to pVIII, and one or more therapeutic genes which could be a DNA encoding a functional p53 protein, or a gene encoding small interfering RNA or microRNA molecules (siRNA or miRNA) that mediate RNA interference for an oncogene such as KRAS has been transfected into the bacterial cell. B. Now, the phagemid, in the presence of the helper phage, is replicated as single stranded DNA and packaged into a filamentous phagemid that is secreted outside of the bacterium. Because the phagmid contains pIII fusions with a targeting ligand, such as TGF-alpha, the phage are able to bind to the target cell (C), enter, release their DNA which then is transcribed into the respective therapeutic molecules and results in an antitumor effect. When administered to a patient with a tumor for which the appropriate receptor has been selected, the bacterium carrying the phagemids results in a therapeutic effect.

8. EXAMPLES

In order to more fully illustrate the invention, the following examples are provided.

8.1. Example 1

Secreted Protease Inhibitors

Secreted protease inhibitors are generated using standard molecular genetic techniques and expressed in bacteria using methods known to those skilled in the arts, operably linking a promoter, ribosomal binding site and initiating methionine if not provided by the first portion of the construct. The construct may either be a plasmid or a chromosomal integration vector, for which many different integration sites exist, including but not limited to any of the attenuation mutations or any of the IS200 elements. The constructs may also be polycistronic, having multiple genes and/or gene products separated by ribosomal binding sites. The different forms of the protease inhibitor constructs are shown in FIG. 2. The constructs used have three basic forms: 1) An N-terminal signal sequence, such as that from M13pIII MKKLLFAIPLVVPFYSHS SEQ ID NO:44, followed by a protease inhibitor such as the furin inhibitor GKRPRAKRA; 2) a protease inhibitor such as the furin inhibitor GKRPRAKRA SEQ ID NO:45 followed by the C-terminal signal sequence of hlyA

SEQ ID NO: 46

STYGSQDYLNPLINEISKIISAAGNLDVKEERSAASLLQLSGNASDFSYGR

NSITLTASA, or 3) a protease inhibitor such as the furin inhibitor GKRPRAKRA SEQ ID NO:47, followed by a furin cleavage signal RXRAKR↓ DL SEQ ID NO:57 followed by the C-terminal signal sequence of hlyA

SEQ ID NO: 48

STYGSQDYLNPLINEISKIISAAGNLDVKEERSAASLLQLSGNASDFSYGR

NSITLTASA

8.2 Example 2

A Targeted Colicin E3 (colE3) Chimera

First, the colicin colE3 immunity protein is synthesized as an expression cassette and cloned into a chromosomal localization vector for an integration site distal to the that of the chimeric effector gene vector described below, e.g., an IS200 deletion vector at location. The amino acid sequence of the immunity protein is given as:

SEQ ID NO: 49

MGLKLDLTWFDKSTEDFKGEEYSKDFGDDGSVMESLGVPFKDNVNNGCFDV

IAEWVPLLQPYFNHQIDISDNEYFVSFDYRDGDW

The sequence is reverse translated using codons optimal for *Salmonella*. The entire chimeric effector protein and expression cassette components are synthesized using standard DNA synthesis techniques at a contract DNA synthesis facility and integrated into the chromosome (Donnenberg and Kaper, 1991, Low et al., 2003, each of which is expressly incorporated herein by reference). The recipient stain can be any tumor-targeted gram-negative bacterium.

This example follows the chimeric pattern shown in FIG. 3A. This chimera is targeted to cancer cells over-expressing EGFR via a TGF-alpha ligand. The chimera consists of the M13 filamentous phage pIII protein 18 amino acid signal sequence, followed by the natural alanine and a 3 glycine spacer. The spacer is followed by the mature 50 amino acid peptide for TGF-alpha, the remaining pIII protein truncated after amino acid 372 of pIII, followed by the enzymatically active (ribonuclease)C-terminus of colicin E3, followed by a stop signal. The complete amino acid sequence is:

SEQ ID NO: 50

MKKLLFAIPLVVPFYSHSAGGGVVSHFNDCPDSHTQFCFHGTCRFLVQEDK

PACVCHSGYVGARCEHADLLAAETVESCLAKSHTENSFTNVWKDDKTLDRY

ANYEGCLWNATGVVVCTGDETQCYGTWVPIGLAIPENEGGGSEGGGSEGGG

SEGGGTKPPEYGDTPIPGYTYINPLDGTYPPGTEQNPANPNPSLEESQPLN

TFMFQNNRFRNRQGALTVYTGTVTQGTDPVKTYYQYTPVSSKAMYDAYWNG

KFRDCAFHSGFNEDLFVCEYQGQSSDLPQPPVNAGGGSGGGSGGGSEGGGS

EGGGSEGGGSEGGGSGGGSGSGDFDYEKMANANKGAMTENADENALQSDAK

GKLDSVATDYGAAIDGFIGDVSGLANGNGATGDFAGSNSQMAQVGDGDNSP

LMNNFRQYLPSLPQSVECRFAHDPMAGGHRMWQMAGLKAQRAQTDVNNKQA

AFDAAAKEKSDADAALSSAMESRKKKEDKKRSAENNLNDEKNKPRKGFKDY

GHDYHPAPKTENIKGLGDLKPGIPKTPKQNGGGKRKRWTGDKGRKIYEWDS

QHGELEGYRASDGQHLGSFDPKTGNQLKGPDPKRNIKKYL*

The entire chimeric effector protein and expression cassette components are synthesized using standard DNA synthesis techniques, for example, at a contract DNA synthesis facility, and cloned into a chromosomal localization vector, e.g., an IS200 deletion vector, and integrated into the chromosome (Donnenberg and Kaper, 1991, Low et al., 2003, each of which is expressly incorporated herein by reference).

8.3 Example 3

A Targeted Colicin Chimera Containing a Lytic Peptide Resulting in Endosomal Release and/or Increased Anti-Cancer Cell Cytotoxicity The lytic peptide PSM-alpha-3 is inserted between the pIII signal sequence and the TGF-alpha (FIG. 3B). The complete sequence of the construct is as follows:

SEQ ID NO: 51

```
MKKLLFAIPLVVPFYSHSAMEFVAKLFKFFKDLLGKFLGNN
VVSHFNDCPDSHTQFCFHGTCRFLVQEDKPACVCHSGYVGARCEHADLLAA
ETVESCLAKSHTENSFTNVWKDDKTLDRYANYEGCLWNATGVVVCTGDETQ
CYGTWVPIGLAIPENEGGGSEGGGSEGGGSEGGGTKPPEYGDTPIPGYTYI
NPLDGTYPPGTEQNPANPNPSLEESQPLNTFMFQNNRFRNRQGALTVYTGT
VTQGTDPVKTYYQYTPVSSKAMYDAYWNGKFRDCAFHSGFNEDLFVCEYQG
QSSDLPQPPVNAGGGSGGGSGGGSEGGGSEGGGSEGGGSEGGGSGGGSGSG
DFDYEKMANANKGAMTENADENALQSDAKGKLDSVATDYGAAIDGFIGDVS
GLANGNGATGDFAGSNSQMAQVGDGDNSPLMNNFRQYLPSLPQSVECRFAH
DPMAGGHRMWQMAGLKAQRAQTDVNNKQAAFDAAAKEKSDADAALSSAMES
RKKKEDKKRSAENNLNDEKNKPRKGFKDYGHDYHPAPKTENIKGLGDLKPG
IPKTPKQNGGGKRKRWTGDKGRKIYEWDSQHGELEGYRASDGQHLGSFDPK
TGNQLKGPDPKRNIKKYL
```

8.4 Example 4

A Chimeric Colicin E7

As for the other colicin E3 constructs, the colicin colE7 immunity protein is synthesized as an expression cassette and cloned into a chromosomal localization vector for an integration site distal to the that of the chimeric effector gene vector described below, e.g., an IS200 deletion vector at location.

The genetic construct of the first colicin E7 chimera follows the same pattern as shown in FIG. 3A, except that the ColE3 C-terminus is replaced with the colE7 (a DNAase)C-terminus comprising amino acids 444 to 576 (FIG. 3C).

The genetic construct of the second colicin E7 chimera follows the same pattern as shown in FIG. 3C, except that the lysis peptide is inserted between the M13pIII signal sequence and the targeting peptide (TGF-alpha) (FIG. 3D).

8.5 Example 5

A Chimeric Colicin Ia

As for the other colicin E3 constructs, the colicin Ia immunity protein is synthesized as an expression cassette and cloned into a chromosomal localization vector for an integration site distal to the that of the chimeric effector gene vector described below, e.g., an IS200 deletion vector at location.

The genetic construct of the first colicin Ia chimera follows the same pattern as shown in FIG. 3A, except that the ColE3 C-terminus is replaced with the Ia (pore forming)C-terminus comprising amino acids 450 to 626 (FIG. 3 E).

The genetic construct of the second colicin Ia chimera follows the same pattern as shown in FIG. 3B, except that the lysis peptide is inserted between the M13pIII signal sequence and the targeting peptide (TGF-alpha) (FIG. 3F).

8.6 Example 6

Expression of a C-Terminal Amidating Enzyme Required to Post-Translationally Modify Gastrin and Bombesin Targeting Peptides A C-terminal amidating enzyme composition known form serum or plasma which comprises a C-terminal amidating enzyme capable of amidating a C-terminal glycine which amidates the carboxy terminus of the C-terminal glycine of a peptide terminating in Gly-Gly. The enzyme participating in such amidation is called peptidylglycine-α-amidating monooxygenase (C-terminal amidating enzyme) (EC.1.14.17.3) (Bradbury et al, Nature, 298, 686, 1982: Glembotski et al, J. Biol, Chem., 259, 6385, 1984, expressly incorporated herein by reference), is considered to catalyze the following reaction:

$$—CHCONHCH_2COOH \rightarrow —CHCONH_2 + \text{glyoxylic acid}$$

is produced by the recombinant.

8.7 Example 7

Expression of Antitumor Lytic Peptides

Examples of antitumor lytic peptides are shown in FIGS. 4A to 4D. It is understood that those peptides utilizing the hlyA signal sequence requires hlyBD in trans together with a functional tolC. The lytic peptide constructs consist of (FIG. 4A) lytic peptide joined to the HlyA signal sequence, (FIG. 4B) lytic peptide, targeting peptide, signals sequence, (FIG. 4C) M13 pIII signal sequence, lytic peptide, M13 pIII amino acids 19 to 372, targeting peptide, (FIG. 4D) M13 signal sequence, lytic peptide, targeting peptide, M13 pIII amino acids 19 to 372.

8.8 Example 8

Expression of Antitumor Lytic Peptide Prodrugs

Examples of antitumor lytic peptide prodrugs are shown in FIGS. 5A to 5D. It is understood that those peptides utilizing the hlyA signal sequence requires hlyBD in trans together with a functional tolC. The lytic peptide prodrug constructs consist of (FIG. 5A) a neutral (e.g., beta sheet) blocking peptide of 50 amino acids, a protease cleavage site shown by downward arrow (for a protease not being blocked by a protease inhibitor), a lytic peptide, and the hlyA signal sequence, which may contain the same protease cleavage site shown by a downward arrow, (FIG. 5B) a neutral (e.g., beta sheet) blocking peptide of 50 amino acids, a lytic peptide, a targeting peptide (e.g., TGF-alpha), a protease cleavage site shown by downward arrow (for a protease not being blocked by a protease inhibitor), and the hlyA signal sequence, which may contain the same protease cleavage site shown by a downward arrow, (FIG. 5C) the M13 pIII signal sequence, a blocking peptide, a protease cleavage sequence, a lytic peptide, M13 pIII amino acids 19 to 372, and a targeting peptide (e.g., TGF-α), and (FIG. 5D) the M13 pIII signal sequence, a blocking peptide, a protease cleavage sequence, a lytic peptide, a targeting peptide (e.g., TGF-alpha), and M13 pIII amino acids 19 to 372.

8.9 Example 9

Cytolethal Distending Toxin cltdB Fusion with Apoptin (FIGS. 6A to 6D)

A cytolethal distending toxin subunit B with tumor-specific nuclear localization and normal cell nuclear export is generated by a fusion with apoptin containing a five glycine linker in between (FIG. 6A). The complete sequence of the construct is as follows:

SEQ ID NO: 52

MKKYIISLIVFLSFYAQADLTDFRVATWNLQGASATTESKWNINVRQLIS

GENAVDILAVQEAGSPPSTAVDTGTLIPSPGIPVRELIWNLSTNSRPQQV

YIYFSAVDALGGRVNLALVSNRRADEVFVLSPVRQGGRPLLGIRIGNDAF

FTAHAIAMRNNDAPALVEEVYNFFRDSRDPVHQALNWMILGDFNREPADL

EMNLTVPVRRASEIISPAAATQTSQRTLDYAVAGNSVAFRPSPLQAGIVY

GARRTQISSDHFPVGVSRRGGGGGMNALQEDTPPGPSTVFRPPTSSRPLE

TPHCREIRIGIAGITITLSLCGCANARAPTLRSATADNSESTGFKNVPDL

RTDQPKPPSKKRSCDPSEYRVSELKESLITTTPSRPRTAKRRIRL 8.10 Example 10

Cytolethal Distending Toxin cltdB Fusion with a Truncated Apoptin

A cytolethal distending toxin subunit B with tumor-specific nuclear localization and normal cell nuclear export is generated by a fusion with a truncated apoptin amino acids 33 to 121 containing a five glycine linker in between (FIG. 6B). The complete sequence of the construct is as follows:

SEQ ID NO: 53

MKKYIISLIVFLSFYAQADLTDFRVATWNLQGASATTESKWNINVRQLIS

GENAVDILAVQEAGSPPSTAVDTGTLIPSPGIPVRELIWNLSTNSRPQQV

YIYFSAVDALGGRVNLALVSNRRADEVFVLSPVRQGGRPLLGIRIGNDAF

FTAHAIAMRNNDAPALVEEVYNFFRDSRDPVHQALNWMILGDFNREPADL

EMNLTVPVRRASEIISPAAATQTSQRTLDYAVAGNSVAFRPSPLQAGIVY

GARRTQISSDHFPVGVSRRGGGGGITPHCREI

RIGIAGITITLSLCGCANARAPTLRSATADNSESTGFKNVPDLRTDQPKP

PSKKRSCDPSEYRVSELKESLITTTPSRPRTAKRRIRL 8.11 Example 11

Cytolethal Distending Toxin cltdB Fusion with a Truncated Apoptin

A cytolethal distending toxin subunit B with tumor-specific nuclear retention signal is generated by a fusion with a truncated apoptin amino acids 33 to 46 containing a five glycine linker in between (FIG. 6C). The complete sequence of the construct is as follows:

SEQ ID NO: 54

MKKYIISLIVFLSFYAQADLTDFRVATWNLQGASATTESKWNINVRQLIS

GENAVDILAVQEAGSPPSTAVDTGTLIPSPGIPVRELIWNLSTNSRPQQV

YIYFSAVDALGGRVNLALVSNRRADEVFVLSPVRQGGRPLLGIRIGNDAF

FTAHAIAMRNNDAPALVEEVYNFFRDSRDPVHQALNWMILGDFNREPADL

EMNLTVPVRRASEIISPAAATQTSQRTLDYAVAGNSVAFRPSPLQAGIVY

GARRTQISSDHFPVGVSRRGGGGGIRIGIAGITITLSL 8.12 Example 12

Cytolethal Distending Toxin cltdB Fusion with a Truncated Apoptin

A cytolethal distending toxin subunit B with a normal cell nuclear export signal is generated by a fusion with a truncated apoptin amino acids 81 to 121 containing a five glycine linker in between (FIG. 6D). The complete sequence of the construct is as follows:

SEQ ID NO: 55

MKKYIISLIVFLSFYAQADLTDFRVATWNLQGASATTESKWNINVRQLIS

GENAVDILAVQEAGSPPSTAVDTGTLIPSPGIPVRELIWNLSTNSRPQQV

YIYFSAVDALGGRVNLALVSNRRADEVFVLSPVRQGGRPLLGIRIGNDAF

FTAHAIAMRNNDAPALVEEVYNFFRDSRDPVHQALNWMILGDFNREPADL

EMNLTVPVRRASEIISPAAATQTSQRTLDYAVAGNSVAFRPSPLQAGIVY

GARRTQISSDHFPVGVSRRGGGGGTDQPKPPSKKRSCDPSEYRVSELKES

LITTTPSRPRTAKRRIRL 8.13 Example 13

Exchange of the Variable Loop in cldtB to Enhance Activity

The amino acid sequence FRDSRDPVHQAL SEQ ID NO:56 which is associated with dimerization and inactivation can be exchanged for the loop NSSSSPPERRVY SEQ ID NO:56 from *Haemophilus* which is associated with stabile retention of cytotoxicity.

8.14 Example 14

Expression of Repeat in Toxin (RTX) Family Members

RTX family members, including *E. coli* hemolysin operon hlyCABD and *Actinobacillus actinomycetemcomitans* leucotoxin 1txCABD are expressed in coordination with protease inhibitors as shown in FIGS. 7A to 7D. *E. coli* hemolysin operon hlyCABD is expressed as a non-chimera (FIG. 7A). *Actinobacillus actinomycetemcomitans* leucotoxin 1txCABD operon is expressed as either a non-hybrid (FIG. 7B) or as a hybrid (FIG. 7C). It is understood that a functional tolC gene is required in the gram-negative bacterial strain for functional expression of each of these operons.

It will be understood that the foregoing is only illustrative of the principles of the invention, and that various modifications can be made by those skilled in the art without departing from the scope and spirit of the invention.

What is claimed is:

1. A method comprising:

coexpressing within, and secreting from, a live genetically engineered bacterium:

(a) at least one heterologous protease sensitive molecule having a protease cleavage site susceptible to cleavage by a non-bacterial protease outside of the bacterium, produced based on a first nucleic acid sequence genetically engineered within the genetically engineered bacterium, and (b) at least one heterologous protease inhibitor peptide, the at least one heterologous protease inhibitor peptide being effective for inhibiting the non-bacterial protease outside of the bacterium from proteolytically degrading the at least one protease sensitive molecule, produced based on a second nucleic acid sequence genetically engineered within the genetically engineered bacterium.

2. The method according to claim 1, wherein the protease sensitive molecule comprises at least one molecule selected from the group consisting of a cytokine, an antibody, a bispecific antibody including single chain antibodies, a chemokine, and the mature form of TGF-alpha.

3. The method according to claim 1, wherein the protease sensitive molecule comprises at least one molecule selected from the group consisting of a toxin, chimeric toxin, a prodrug converting enzyme, colicin, cytolethal distending toxin (cldt), cytotoxic nectrotic factor (cnf), dermonecrotic factor (dmf), shiga toxin, shiga-like toxin, *Pseudomonas* ToxA, colicin colE3, colicin colE7, colicin col-Ia, membrane lytic peptides from *Staphalococcus*, leucotoxin, leuckotoxin: HlyA hybrid, heat stable enterotoxin, autotransporter toxin picU, autotransporter toxin espC, autotransporter toxin sat, chlostridium enterotoxin, aerolysin, typhoid toxin, subtilase, *Bordetella* adenylate cyclase toxin, pertussus toxin, and porB.

4. The method according to claim 1, wherein the protease sensitive molecule comprises at least one molecule selected from the group consisting of cytolethal distending toxin (cldt) and typhoid toxin fused to a peptide containing the nuclear localization signal from apoptin.

5. The method according to claim 1, wherein the protease sensitive molecule is a chimeric molecule having at least a toxic functionality, a protease cleavage site, and a targeting functionality.

6. The method according to claim 1, wherein the protease sensitive molecule is a chimeric molecule having at least a toxic functionality, a protease cleavage site, and a targeting functionality, and wherein the protease inhibitor peptide expressed and secreted by the live genetically engineered bacterium is effective to reduce proteolytic degradation of the protease sensitive molecule by a serine protease outside of the live genetically engineered bacterium.

7. The method according to claim 1, wherein the protease sensitive molecule comprises a chimeric colicin, in which targeting and translocation sequences of the colicin are replaced with an M13 pIII signal sequence and a targeting peptide, followed by a membrane anchor-truncated M13 pIII, and the C-terminal catalytic portion of the colicin.

8. The method according to claim 7, wherein a *Staphalococcus* lytic peptide is inserted between the M13 pIII signal sequence and the targeting peptide.

9. The method according to claim 1, where the protease inhibitor peptide selectively inhibits furin.

10. The method according to claim 1, wherein the live genetically engineered bacterium is genetically engineered to deliver a therapeutic RNA molecule comprising at least one of a small interfering RNA (siRNA) and micro RNA (miRNA).

11. The method according to claim 1, wherein the genetically engineered live bacteria is adapted to selectively replicate in and colonize a selected tissue type within a mammal in which the non-bacterial protease is present, and concurrently secrete within the selected tissue type the at least one protease sensitive molecule, and the at least one protease inhibitor peptide.

12. The method according to claim 8, wherein the toxin that has at least one protease-sensitive cytotoxic molecule is *Pseudomonas* ToxA.

13. A method comprising:

providing a live bacterium, genetically engineered to have at least a first heterologous nucleic acid and a second heterologous nucleic acid, which selectively replicates within a target tissue of an animal;

expressing, within the genetically engineered live bacteria, a first gene product corresponding to the first heterologous nucleic acid, and a second gene product corresponding to the second heterologous nucleic acid; and secreting from the genetically engineered live bacteria, within the target tissue of the animal, the first gene product and the second gene product, wherein the first gene product comprises at least one heterologous protease sensitive cytotoxic molecule having a protease cleavage site susceptible to cleavage by a non-bacterial protease found within the animal, and wherein the second gene product comprises at least one heterologous protease inhibitor peptide effective for inhibiting the non-bacterial protease found within the animal from proteolytically degrading the secreted at least one protease sensitive cytotoxic molecule within the target tissue, such that the at least one heterologous protease sensitive cytotoxic molecule is preserved within the target tissue and has a cytotoxic effect within the target tissue, and is degraded by the protease outside the target tissue.

14. A method comprising:

providing a live genetically engineered bacterium;

coexpressing within, and secreting into an environment from, the live genetically engineered bacterium:

(a) at least one protease sensitive molecule having at least one protease cleavage site susceptible to cleavage by a protease within the environment not secreted by the genetically engineered live bacterium, and (b) at least one heterologous protease inhibitor peptide effective for inhibiting the protease within the environment from proteolytically degrading the at least one protease sensitive molecule nearby the live genetically engineered bacterium in the environment.

15. The method according to claim 14, wherein:

the environment comprises an organ of an animal or human;

the at least one protease sensitive molecule comprises a therapeutic domain having a desired effect within the organ and an undesired effect outside of the organ;

further comprising secreting the at least one heterologous protease inhibitor in an effective amount to inhibit proteolysis of the therapeutic domain within the organ, to achieve the desired effect, and in an amount sufficiently limited to permit proteolysis of the therapeutic domain by the protease outside of the organ to diminish the undesired effect.

16. The method according to claim 15, wherein the at least one protease sensitive molecule further comprises a bacterial secretion facilitator, wherein the protease cleavage site is located within the such that proteolysis by the protease at the protease cleavage site diminishes the desired effect of the therapeutic domain.

17. The method according to claim 14, wherein the at least one protease sensitive molecule has a plurality of protease cleavage sites susceptible to cleavage by at least one protease within the environment.

18. The method according to claim 14, wherein the at least one protease sensitive molecule has a plurality of different types of protease cleavage sites susceptible to cleavage by at least two different proteases within the environment.

19. The method according to claim 14, wherein the at least one heterologous protease inhibitor comprises a plurality of different types of protease inhibitors, adapted to inhibit different proteases.

20. The method according to claim 14, wherein the at least one heterologous protease inhibitor comprises an alternating series comprising a plurality of protease inhibition sites and a plurality of protease cleavage sites.

* * * * *

SEQUENCE LISTING

```
<160> NUMBER OF SEQ ID NOS: 60

<210> SEQ ID NO 1
<211> LENGTH: 36
<212> TYPE: PRT
<213> ORGANISM: Artificial Sequence
<220> FEATURE:
<223> OTHER INFORMATION: FURIN INHIBITOR

<400> SEQUENCE: 1

Pro Ala Ala Ala Thr Val Thr Lys Lys Val Ala Lys Ser Pro Lys Lys
1               5                   10                  15

Ala Lys Ala Ala Lys Pro Lys Lys Ala Ala Lys Ser Ala Ala Lys Ala
            20                  25                  30

Val Lys Pro Lys
        35


<210> SEQ ID NO 2
<211> LENGTH: 14
<212> TYPE: PRT
<213> ORGANISM: Artificial Sequence
<220> FEATURE:
<223> OTHER INFORMATION: FURIN INHIBITOR

<400> SEQUENCE: 2

Thr Lys Lys Val Ala Lys Arg Pro Arg Ala Lys Arg Ala Ala
1               5                   10


<210> SEQ ID NO 3
<211> LENGTH: 14
<212> TYPE: PRT
<213> ORGANISM: Artificial Sequence
<220> FEATURE:
<223> OTHER INFORMATION: FURIN INHIBITOR

<400> SEQUENCE: 3

Thr Lys Lys Val Ala Lys Arg Pro Arg Ala Lys Arg Asp Leu
1               5                   10


<210> SEQ ID NO 4
<211> LENGTH: 9
<212> TYPE: PRT
<213> ORGANISM: Artificial Sequence
<220> FEATURE:
<223> OTHER INFORMATION: FURIN INHIBITOR

<400> SEQUENCE: 4

Gly Lys Arg Pro Arg Ala Lys Arg Ala
1               5


<210> SEQ ID NO 5
<211> LENGTH: 10
<212> TYPE: PRT
<213> ORGANISM: Artificial Sequence
<220> FEATURE:
<223> OTHER INFORMATION: FURIN INHIBITOR

<400> SEQUENCE: 5

Cys Lys Arg Pro Arg Ala Lys Arg Asp Leu
1               5                   10


<210> SEQ ID NO 6
<211> LENGTH: 12
<212> TYPE: PRT
<213> ORGANISM: Artificial Sequence
<220> FEATURE:
```

-continued

<223> OTHER INFORMATION: FURIN INHIBITOR

<400> SEQUENCE: 6

Cys Val Ala Lys Arg Pro Arg Ala Lys Arg Asp Leu
1 5 10

<210> SEQ ID NO 7
<211> LENGTH: 14
<212> TYPE: PRT
<213> ORGANISM: Artificial Sequence
<220> FEATURE:
<223> OTHER INFORMATION: FURIN INHIBITOR

<400> SEQUENCE: 7

Cys Lys Lys Val Ala Lys Arg Pro Arg Ala Lys Arg Asp Leu
1 5 10

<210> SEQ ID NO 8
<211> LENGTH: 6
<212> TYPE: PRT
<213> ORGANISM: Artificial Sequence
<220> FEATURE:
<223> OTHER INFORMATION: FURIN INHIBITOR

<400> SEQUENCE: 8

Arg Arg Arg Arg Arg Arg
1 5

<210> SEQ ID NO 9
<211> LENGTH: 10
<212> TYPE: PRT
<213> ORGANISM: Artificial Sequence
<220> FEATURE:
<223> OTHER INFORMATION: KALLIKREIN 2 INHIBITOR

<400> SEQUENCE: 9

Ser Arg Phe Lys Val Trp Trp Ala Ala Gly
1 5 10

<210> SEQ ID NO 10
<211> LENGTH: 10
<212> TYPE: PRT
<213> ORGANISM: Artificial Sequence
<220> FEATURE:
<223> OTHER INFORMATION: KALLIKREIN 2 INHIBITOR

<400> SEQUENCE: 10

Ala Ala Arg Arg Pro Phe Pro Ala Pro Ser
1 5 10

<210> SEQ ID NO 11
<211> LENGTH: 10
<212> TYPE: PRT
<213> ORGANISM: Artificial Sequence
<220> FEATURE:
<223> OTHER INFORMATION: KALLIKREIN 2 INHIBITOR

<400> SEQUENCE: 11

Pro Ala Arg Arg Pro Phe Pro Val Thr Ala
1 5 10

<210> SEQ ID NO 12
<211> LENGTH: 56
<212> TYPE: PRT
<213> ORGANISM: Artificial Sequence
<220> FEATURE:
<223> OTHER INFORMATION: TISSUE PROTEASE INHIBITOR

<400> SEQUENCE: 12

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 13
<211> LENGTH: 15
<212> TYPE: PRT
<213> ORGANISM: Artificial Sequence
<220> FEATURE:
<223> OTHER INFORMATION: TARGETING PEPTIDE CG-BETA

<400> SEQUENCE: 13

Ser Tyr Ala Val Ala Leu Ser Cys Gln Cys Ala Leu Cys Arg Arg
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: TARGETING PEPTIDE CG-BETA (ALA TRUNCATION)

<400> SEQUENCE: 14

Ala Val Ala Leu Ser Cys Gln Cys Ala Leu Cys Arg Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: LHRH

<400> SEQUENCE: 15

Glu His Trp Ser Tyr Gly Leu Arg Pro Gly
1               5                   10

<210> SEQ ID NO 16
<211> LENGTH: 8
<212> TYPE: PRT
<213> ORGANISM: Artificial Sequence
<220> FEATURE:
<223> OTHER INFORMATION: SOMATOSTATIN OCTAPEPTIDE RC-121

<400> SEQUENCE: 16

Phe Cys Tyr Trp Lys Val Cys Thr
1               5

<210> SEQ ID NO 17
<211> LENGTH: 14
<212> TYPE: PRT
<213> ORGANISM: Artificial Sequence
<220> FEATURE:
<223> OTHER INFORMATION: PROAPOPTOTIC PEPTIDE

<400> SEQUENCE: 17

Lys Leu Ala Lys Leu Ala Lys Lys Leu Ala Leu Lys Leu Ala
1               5                   10

<210> SEQ ID NO 18
<211> LENGTH: 19
<212> TYPE: PRT
<213> ORGANISM: Escherichia coli

<400> SEQUENCE: 18

Asn Ser Ser Asn Tyr Cys Cys Glu Leu Cys Cys Asn Pro Ala Cys Thr
1 5 10 15

Gly Cys Tyr

<210> SEQ ID NO 19
<211> LENGTH: 61
<212> TYPE: PRT
<213> ORGANISM: Escherichia coli

<400> SEQUENCE: 19

Val Leu Ser Phe Ser Pro Phe Ala Gln Asp Ala Lys Pro Val Glu Ser
1 5 10 15

Ser Lys Glu Lys Ile Thr Leu Glu Ser Lys Lys Cys Asn Ile Ala Lys
20 25 30

Lys Ser Asn Lys Ser Asp Pro Glu Ser Met Asn Ser Ser Asn Tyr Cys
35 40 45

Cys Glu Leu Cys Cys Asn Pro Ala Cys Thr Gly Cys Tyr
50 55 60

<210> SEQ ID NO 20
<211> LENGTH: 9
<212> TYPE: PRT
<213> ORGANISM: Artificial Sequence
<220> FEATURE:
<223> OTHER INFORMATION: TARGETS V-BETA3 INTEGRIN

<400> SEQUENCE: 20

Cys Asp Cys Arg Gly Asp Cys Phe Cys
1 5

<210> SEQ ID NO 21
<211> LENGTH: 6
<212> TYPE: PRT
<213> ORGANISM: Artificial Sequence
<220> FEATURE:
<223> OTHER INFORMATION: N-TERMINAL TRUNCATION OF GASTRIN

<400> SEQUENCE: 21

Met Gly Trp Met Asp Phe
1 5

<210> SEQ ID NO 22
<211> LENGTH: 27
<212> TYPE: PRT
<213> ORGANISM: Artificial Sequence
<220> FEATURE:
<223> OTHER INFORMATION: GASTRIN RELEASING PEPTIDE

<400> SEQUENCE: 22

Val Pro Leu Pro Ala Gly Gly Gly Thr Val Leu Thr Lys Met Tyr Pro
1 5 10 15

Arg Gly Asn His Trp Ala Val Gly His Leu Met
20 25

<210> SEQ ID NO 23
<211> LENGTH: 8

-continued

<212> TYPE: PRT
<213> ORGANISM: Artificial Sequence
<220> FEATURE:
<223> OTHER INFORMATION: TARGETS AML

<400> SEQUENCE: 23

Cys Ala Tyr His Leu Arg Arg Cys
1               5

<210> SEQ ID NO 24
<211> LENGTH: 3
<212> TYPE: PRT
<213> ORGANISM: Artificial Sequence
<220> FEATURE:
<223> OTHER INFORMATION: LYMPH NODE HOMING

<400> SEQUENCE: 24

Cys Ala Tyr
1

<210> SEQ ID NO 25
<211> LENGTH: 4
<212> TYPE: PRT
<213> ORGANISM: Artificial Sequence
<220> FEATURE:
<223> OTHER INFORMATION: CELL PENETRATING

<400> SEQUENCE: 25

Arg Leu Arg Arg
1

<210> SEQ ID NO 26
<211> LENGTH: 7
<212> TYPE: PRT
<213> ORGANISM: Artificial Sequence
<220> FEATURE:
<223> OTHER INFORMATION: TARGETS COLONIC DYSPLASIA

<400> SEQUENCE: 26

Val Arg Pro Met Pro Leu Gln
1               5

<210> SEQ ID NO 27
<211> LENGTH: 7
<212> TYPE: PRT
<213> ORGANISM: Artificial Sequence
<220> FEATURE:
<223> OTHER INFORMATION: BINDS IRRADIATED TUMORS

<400> SEQUENCE: 27

His Val Gly Gly Ser Ser Val
1               5

<210> SEQ ID NO 28
<211> LENGTH: 13
<212> TYPE: PRT
<213> ORGANISM: Artificial Sequence
<220> FEATURE:
<223> OTHER INFORMATION: BINDS MEMBRANE DIPEPTIDASE (MDP)

<400> SEQUENCE: 28

Cys Gly Phe Glu Cys Val Arg Gln Cys Pro Glu Arg Cys
1               5                   10

<210> SEQ ID NO 29
<211> LENGTH: 7
<212> TYPE: PRT

-continued

<213> ORGANISM: Artificial Sequence
<220> FEATURE:
<223> OTHER INFORMATION: TARGETS MURINE PROSTATE VASCULATURE

<400> SEQUENCE: 29

Ser Met Ser Ile Ala Arg Leu
1 5

<210> SEQ ID NO 30
<211> LENGTH: 7
<212> TYPE: PRT
<213> ORGANISM: Artificial Sequence
<220> FEATURE:
<223> OTHER INFORMATION: TARGETS MURINE PROSTATE VASCULATURE

<400> SEQUENCE: 30

Val Ser Phe Leu Glu Tyr Arg
1 5

<210> SEQ ID NO 31
<211> LENGTH: 32
<212> TYPE: PRT
<213> ORGANISM: Artificial Sequence
<220> FEATURE:
<223> OTHER INFORMATION: FRAGMENT OF THE HIGH MOBILITY GROUP (HMG) N2

<400> SEQUENCE: 31

Cys Lys Asp Glu Pro Gln Arg Arg Ser Ala Arg Leu Ser Ala Lys Pro
1 5 10 15

Ala Pro Pro Lys Pro Glu Pro Lys Pro Lys Lys Ala Pro Ala Lys Lys
20 25 30

<210> SEQ ID NO 32
<211> LENGTH: 19
<212> TYPE: PRT
<213> ORGANISM: Artificial Sequence
<220> FEATURE:
<223> OTHER INFORMATION: VEGF BINDING PEPTIDE

<400> SEQUENCE: 32

Val Glu Pro Asn Cys Asp Ile His Val Met Trp Glu Trp Glu Cys Phe
1 5 10 15

Glu Arg Leu

<210> SEQ ID NO 33
<211> LENGTH: 12
<212> TYPE: PRT
<213> ORGANISM: Artificial Sequence
<220> FEATURE:
<223> OTHER INFORMATION: NASOPHYRINGIAL DERIV ED L-PEPTIDE, CAUSES
INTERNALIZATION OF PHAGE

<400> SEQUENCE: 33

Arg Leu Leu Asp Thr Asn Arg Pro Leu Leu Pro Tyr
1 5 10

<210> SEQ ID NO 34
<211> LENGTH: 20
<212> TYPE: PRT
<213> ORGANISM: Artificial Sequence
<220> FEATURE:
<223> OTHER INFORMATION: RGDLATL TRUNCATED, TARGETS ALPHA(V) BETA(6)
INTEGRIN

<400> SEQUENCE: 34

Arg Gly Asp Leu Ala Thr Leu Arg Gln Leu Ala Gln Glu Asp Gly Val

```
1               5                   10                  15

Val Gly Val Arg
            20


<210> SEQ ID NO 35
<211> LENGTH: 26
<212> TYPE: PRT
<213> ORGANISM: Staphylococcus aureus

<400> SEQUENCE: 35

Met Ala Gln Asp Ile Ile Ser Thr Ile Ser Asp Leu Val Lys Trp Ile
1               5                   10                  15

Ile Asp Thr Val Asn Lys Phe Thr Lys Lys
            20                  25


<210> SEQ ID NO 36
<211> LENGTH: 26
<212> TYPE: PRT
<213> ORGANISM: Staphylococcus epidermidis

<400> SEQUENCE: 36

Met Met Ala Ala Asp Ile Ile Ser Thr Ile Gly Asp Leu Val Lys Trp
1               5                   10                  15

Ile Ile Asp Thr Val Asn Lys Phe Lys Lys
            20                  25


<210> SEQ ID NO 37
<211> LENGTH: 26
<212> TYPE: PRT
<213> ORGANISM: Staphylococcus aureus

<400> SEQUENCE: 37

Met Ala Gln Asp Ile Ile Ser Thr Ile Ser Asp Leu Val Lys Trp Ile
1               5                   10                  15

Ile Asp Thr Val Asn Lys Phe Thr Lys Lys
            20                  25


<210> SEQ ID NO 38
<211> LENGTH: 21
<212> TYPE: PRT
<213> ORGANISM: Staphylococcus aureus

<400> SEQUENCE: 38

Met Gly Ile Ile Ala Gly Ile Ile Lys Val Ile Lys Ser Leu Ile Glu
1               5                   10                  15

Gln Phe Thr Gly Lys
            20


<210> SEQ ID NO 39
<211> LENGTH: 21
<212> TYPE: PRT
<213> ORGANISM: Staphylococcus aureus

<400> SEQUENCE: 39

Met Gly Ile Ile Ala Gly Ile Ile Lys Phe Ile Lys Gly Leu Ile Glu
1               5                   10                  15

Lys Phe Thr Gly Lys
            20


<210> SEQ ID NO 40
<211> LENGTH: 22
<212> TYPE: PRT
```

<213> ORGANISM: Staphylococcus aureus

<400> SEQUENCE: 40

```
Met Glu Phe Val Ala Lys Leu Phe Lys Phe Phe Lys Asp Leu Leu Gly
1               5                   10                  15

Lys Phe Leu Gly Asn Asn
            20
```

<210> SEQ ID NO 41
<211> LENGTH: 20
<212> TYPE: PRT
<213> ORGANISM: Staphylococcus aureus

<400> SEQUENCE: 41

```
Met Ala Ile Val Gly Thr Ile Ile Lys Ile Ile Lys Ala Ile Ile Asp
1               5                   10                  15

Ile Phe Ala Lys
            20
```

<210> SEQ ID NO 42
<211> LENGTH: 44
<212> TYPE: PRT
<213> ORGANISM: Staphylococcus aureus

<400> SEQUENCE: 42

```
Met Glu Gly Leu Phe Asn Ala Ile Lys Asp Thr Val Thr Ala Ala Ile
1               5                   10                  15

Asn Asn Asp Gly Ala Lys Leu Gly Thr Ser Ile Val Ser Ile Val Glu
            20                  25                  30

Asn Gly Val Gly Leu Leu Gly Lys Leu Phe Gly Phe
        35                  40
```

<210> SEQ ID NO 43
<211> LENGTH: 44
<212> TYPE: PRT
<213> ORGANISM: Staphylococcus aureus

<400> SEQUENCE: 43

```
Met Thr Gly Leu Ala Glu Ala Ile Ala Asn Thr Val Gln Ala Ala Gln
1               5                   10                  15

Gln His Asp Ser Val Lys Leu Gly Thr Ser Ile Val Asp Ile Val Ala
            20                  25                  30

Asn Gly Val Gly Leu Leu Gly Lys Leu Phe Gly Phe
        35                  40
```

<210> SEQ ID NO 44
<211> LENGTH: 18
<212> TYPE: PRT
<213> ORGANISM: Artificial Sequence
<220> FEATURE:
<223> OTHER INFORMATION: M13pIII N-TERMINAL SEQUENCE

<400> SEQUENCE: 44

```
Met Lys Lys Leu Leu Phe Ala Ile Pro Leu Val Val Pro Phe Tyr Ser
1               5                   10                  15

His Ser
```

<210> SEQ ID NO 45
<211> LENGTH: 9
<212> TYPE: PRT
<213> ORGANISM: Artificial Sequence
<220> FEATURE:

-continued

<223> OTHER INFORMATION: FURIN INHIBITOR

<400> SEQUENCE: 45

Gly Lys Arg Pro Arg Ala Lys Arg Ala
1 5

<210> SEQ ID NO 46
<211> LENGTH: 60
<212> TYPE: PRT
<213> ORGANISM: Artificial Sequence
<220> FEATURE:
<223> OTHER INFORMATION: C-TERMINAL SIGNAL SEQUENCE OF hly-A

<400> SEQUENCE: 46

Ser Thr Tyr Gly Ser Gln Asp Tyr Leu Asn Pro Leu Ile Asn Glu Ile
1 5 10 15

Ser Lys Ile Ile Ser Ala Ala Gly Asn Leu Asp Val Lys Glu Glu Arg
20 25 30

Ser Ala Ala Ser Leu Leu Gln Leu Ser Gly Asn Ala Ser Asp Phe Ser
35 40 45

Tyr Gly Arg Asn Ser Ile Thr Leu Thr Ala Ser Ala
50 55 60

<210> SEQ ID NO 47
<211> LENGTH: 9
<212> TYPE: PRT
<213> ORGANISM: Artificial Sequence
<220> FEATURE:
<223> OTHER INFORMATION: FURIN INHIBITOR

<400> SEQUENCE: 47

Gly Lys Arg Pro Arg Ala Lys Arg Ala
1 5

<210> SEQ ID NO 48
<211> LENGTH: 60
<212> TYPE: PRT
<213> ORGANISM: Artificial Sequence
<220> FEATURE:
<223> OTHER INFORMATION: C-TERMINAL SIGNAL SEQUENCE OF hlyA

<400> SEQUENCE: 48

Ser Thr Tyr Gly Ser Gln Asp Tyr Leu Asn Pro Leu Ile Asn Glu Ile
1 5 10 15

Ser Lys Ile Ile Ser Ala Ala Gly Asn Leu Asp Val Lys Glu Glu Arg
20 25 30

Ser Ala Ala Ser Leu Leu Gln Leu Ser Gly Asn Ala Ser Asp Phe Ser
35 40 45

Tyr Gly Arg Asn Ser Ile Thr Leu Thr Ala Ser Ala
50 55 60

<210> SEQ ID NO 49
<211> LENGTH: 85
<212> TYPE: PRT
<213> ORGANISM: Artificial Sequence
<220> FEATURE:
<223> OTHER INFORMATION: IMMUNITY PROTEIN

<400> SEQUENCE: 49

Met Gly Leu Lys Leu Asp Leu Thr Trp Phe Asp Lys Ser Thr Glu Asp
1 5 10 15

Phe Lys Gly Glu Glu Tyr Ser Lys Asp Phe Gly Asp Asp Gly Ser Val
20 25 30

```
Met Glu Ser Leu Gly Val Pro Phe Lys Asp Asn Val Asn Asn Gly Cys
        35                  40                  45

Phe Asp Val Ile Ala Glu Trp Val Pro Leu Leu Gln Pro Tyr Phe Asn
    50                  55                  60

His Gln Ile Asp Ile Ser Asp Asn Glu Tyr Phe Val Ser Phe Asp Tyr
65                  70                  75                  80

Arg Asp Gly Asp Trp
                85


<210> SEQ ID NO 50
<211> LENGTH: 601
<212> TYPE: PRT
<213> ORGANISM: Artificial Sequence
<220> FEATURE:
<223> OTHER INFORMATION: CHIMERIC PATTERN:
      M13pIII(18)-Ala-Gly-Gly-Gly-TGF-alpha(50)-M13pIII(372+)-C-terminus
      of colicin E3

<400> SEQUENCE: 50

Met Lys Lys Leu Leu Phe Ala Ile Pro Leu Val Val Pro Phe Tyr Ser
1               5                   10                  15

His Ser Ala Gly Gly Gly Val Val Ser His Phe Asn Asp Cys Pro Asp
            20                  25                  30

Ser His Thr Gln Phe Cys Phe His Gly Thr Cys Arg Phe Leu Val Gln
        35                  40                  45

Glu Asp Lys Pro Ala Cys Val Cys His Ser Gly Tyr Val Gly Ala Arg
    50                  55                  60

Cys Glu His Ala Asp Leu Leu Ala Ala Glu Thr Val Glu Ser Cys Leu
65                  70                  75                  80

Ala Lys Ser His Thr Glu Asn Ser Phe Thr Asn Val Trp Lys Asp Asp
                85                  90                  95

Lys Thr Leu Asp Arg Tyr Ala Asn Tyr Glu Gly Cys Leu Trp Asn Ala
            100                 105                 110

Thr Gly Val Val Val Cys Thr Gly Asp Glu Thr Gln Cys Tyr Gly Thr
        115                 120                 125

Trp Val Pro Ile Gly Leu Ala Ile Pro Glu Asn Glu Gly Gly Gly Ser
    130                 135                 140

Glu Gly Gly Gly Ser Glu Gly Gly Gly Ser Glu Gly Gly Gly Thr Lys
145                 150                 155                 160

Pro Pro Glu Tyr Gly Asp Thr Pro Ile Pro Gly Tyr Thr Tyr Ile Asn
                165                 170                 175

Pro Leu Asp Gly Thr Tyr Pro Pro Gly Thr Glu Gln Asn Pro Ala Asn
            180                 185                 190

Pro Asn Pro Ser Leu Glu Glu Ser Gln Pro Leu Asn Thr Phe Met Phe
        195                 200                 205

Gln Asn Asn Arg Phe Arg Asn Arg Gln Gly Ala Leu Thr Val Tyr Thr
    210                 215                 220

Gly Thr Val Thr Gln Gly Thr Asp Pro Val Lys Thr Tyr Tyr Gln Tyr
225                 230                 235                 240

Thr Pro Val Ser Ser Lys Ala Met Tyr Asp Ala Tyr Trp Asn Gly Lys
                245                 250                 255

Phe Arg Asp Cys Ala Phe His Ser Gly Phe Asn Glu Asp Leu Phe Val
            260                 265                 270

Cys Glu Tyr Gln Gly Gln Ser Ser Asp Leu Pro Gln Pro Pro Val Asn
        275                 280                 285
```

-continued

```
Ala Gly Gly Gly Ser Gly Gly Gly Ser Gly Gly Gly Ser Glu Gly Gly
    290                 295                 300

Gly Ser Glu Gly Gly Gly Ser Glu Gly Gly Gly Ser Glu Gly Gly Gly
305                 310                 315                 320

Ser Gly Gly Gly Ser Gly Ser Gly Asp Phe Asp Tyr Glu Lys Met Ala
                325                 330                 335

Asn Ala Asn Lys Gly Ala Met Thr Glu Asn Ala Asp Glu Asn Ala Leu
            340                 345                 350

Gln Ser Asp Ala Lys Gly Lys Leu Asp Ser Val Ala Thr Asp Tyr Gly
        355                 360                 365

Ala Ala Ile Asp Gly Phe Ile Gly Asp Val Ser Gly Leu Ala Asn Gly
    370                 375                 380

Asn Gly Ala Thr Gly Asp Phe Ala Gly Ser Asn Ser Gln Met Ala Gln
385                 390                 395                 400

Val Gly Asp Gly Asp Asn Ser Pro Leu Met Asn Asn Phe Arg Gln Tyr
                405                 410                 415

Leu Pro Ser Leu Pro Gln Ser Val Glu Cys Arg Phe Ala His Asp Pro
            420                 425                 430

Met Ala Gly Gly His Arg Met Trp Gln Met Ala Gly Leu Lys Ala Gln
        435                 440                 445

Arg Ala Gln Thr Asp Val Asn Asn Lys Gln Ala Ala Phe Asp Ala Ala
    450                 455                 460

Ala Lys Glu Lys Ser Asp Ala Asp Ala Ala Leu Ser Ser Ala Met Glu
465                 470                 475                 480

Ser Arg Lys Lys Lys Glu Asp Lys Lys Arg Ser Ala Glu Asn Asn Leu
                485                 490                 495

Asn Asp Glu Lys Asn Lys Pro Arg Lys Gly Phe Lys Asp Tyr Gly His
            500                 505                 510

Asp Tyr His Pro Ala Pro Lys Thr Glu Asn Ile Lys Gly Leu Gly Asp
        515                 520                 525

Leu Lys Pro Gly Ile Pro Lys Thr Pro Lys Gln Asn Gly Gly Gly Lys
    530                 535                 540

Arg Lys Arg Trp Thr Gly Asp Lys Gly Arg Lys Ile Tyr Glu Trp Asp
545                 550                 555                 560

Ser Gln His Gly Glu Leu Glu Gly Tyr Arg Ala Ser Asp Gly Gln His
                565                 570                 575

Leu Gly Ser Phe Asp Pro Lys Thr Gly Asn Gln Leu Lys Gly Pro Asp
            580                 585                 590

Pro Lys Arg Asn Ile Lys Lys Tyr Leu
        595                 600


<210> SEQ ID NO 51
<211> LENGTH: 620
<212> TYPE: PRT
<213> ORGANISM: Artificial Sequence
<220> FEATURE:
<223> OTHER INFORMATION: CHIMERIC PROTEIN: M13pIII-PSM-alpha-3-TGF-alpha

<400> SEQUENCE: 51

Met Lys Lys Leu Leu Phe Ala Ile Pro Leu Val Val Pro Phe Tyr Ser
1               5                   10                  15

His Ser Ala Met Glu Phe Val Ala Lys Leu Phe Lys Phe Phe Lys Asp
            20                  25                  30

Leu Leu Gly Lys Phe Leu Gly Asn Asn Val Val Ser His Phe Asn Asp
        35                  40                  45
```

-continued

```
Cys Pro Asp Ser His Thr Gln Phe Cys Phe His Gly Thr Cys Arg Phe
    50                  55                  60

Leu Val Gln Glu Asp Lys Pro Ala Cys Val Cys His Ser Gly Tyr Val
65                  70                  75                  80

Gly Ala Arg Cys Glu His Ala Asp Leu Leu Ala Ala Glu Thr Val Glu
                85                  90                  95

Ser Cys Leu Ala Lys Ser His Thr Glu Asn Ser Phe Thr Asn Val Trp
            100                 105                 110

Lys Asp Asp Lys Thr Leu Asp Arg Tyr Ala Asn Tyr Glu Gly Cys Leu
        115                 120                 125

Trp Asn Ala Thr Gly Val Val Val Cys Thr Gly Asp Glu Thr Gln Cys
    130                 135                 140

Tyr Gly Thr Trp Val Pro Ile Gly Leu Ala Ile Pro Glu Asn Glu Gly
145                 150                 155                 160

Gly Gly Ser Glu Gly Gly Gly Ser Glu Gly Gly Gly Ser Glu Gly Gly
                165                 170                 175

Gly Thr Lys Pro Pro Glu Tyr Gly Asp Thr Pro Ile Pro Gly Tyr Thr
            180                 185                 190

Tyr Ile Asn Pro Leu Asp Gly Thr Tyr Pro Pro Gly Thr Glu Gln Asn
        195                 200                 205

Pro Ala Asn Pro Asn Pro Ser Leu Glu Glu Ser Gln Pro Leu Asn Thr
    210                 215                 220

Phe Met Phe Gln Asn Asn Arg Phe Arg Asn Arg Gln Gly Ala Leu Thr
225                 230                 235                 240

Val Tyr Thr Gly Thr Val Thr Gln Gly Thr Asp Pro Val Lys Thr Tyr
                245                 250                 255

Tyr Gln Tyr Thr Pro Val Ser Ser Lys Ala Met Tyr Asp Ala Tyr Trp
            260                 265                 270

Asn Gly Lys Phe Arg Asp Cys Ala Phe His Ser Gly Phe Asn Glu Asp
        275                 280                 285

Leu Phe Val Cys Glu Tyr Gln Gly Gln Ser Ser Asp Leu Pro Gln Pro
    290                 295                 300

Pro Val Asn Ala Gly Gly Gly Ser Gly Gly Gly Ser Gly Gly Gly Ser
305                 310                 315                 320

Glu Gly Gly Gly Ser Glu Gly Gly Gly Ser Glu Gly Gly Gly Ser Glu
                325                 330                 335

Gly Gly Gly Ser Gly Gly Gly Ser Gly Ser Gly Asp Phe Asp Tyr Glu
            340                 345                 350

Lys Met Ala Asn Ala Asn Lys Gly Ala Met Thr Glu Asn Ala Asp Glu
        355                 360                 365

Asn Ala Leu Gln Ser Asp Ala Lys Gly Lys Leu Asp Ser Val Ala Thr
    370                 375                 380

Asp Tyr Gly Ala Ala Ile Asp Gly Phe Ile Gly Asp Val Ser Gly Leu
385                 390                 395                 400

Ala Asn Gly Asn Gly Ala Thr Gly Asp Phe Ala Gly Ser Asn Ser Gln
                405                 410                 415

Met Ala Gln Val Gly Asp Gly Asp Asn Ser Pro Leu Met Asn Asn Phe
            420                 425                 430

Arg Gln Tyr Leu Pro Ser Leu Pro Gln Ser Val Glu Cys Arg Phe Ala
        435                 440                 445

His Asp Pro Met Ala Gly Gly His Arg Met Trp Gln Met Ala Gly Leu
    450                 455                 460

Lys Ala Gln Arg Ala Gln Thr Asp Val Asn Asn Lys Gln Ala Ala Phe
```

```
465                 470                 475                 480

Asp Ala Ala Ala Lys Glu Lys Ser Asp Ala Asp Ala Ala Leu Ser Ser
                485                 490                 495

Ala Met Glu Ser Arg Lys Lys Lys Glu Asp Lys Lys Arg Ser Ala Glu
            500                 505                 510

Asn Asn Leu Asn Asp Glu Lys Asn Lys Pro Arg Lys Gly Phe Lys Asp
        515                 520                 525

Tyr Gly His Asp Tyr His Pro Ala Pro Lys Thr Glu Asn Ile Lys Gly
    530                 535                 540

Leu Gly Asp Leu Lys Pro Gly Ile Pro Lys Thr Pro Lys Gln Asn Gly
545                 550                 555                 560

Gly Gly Lys Arg Lys Arg Trp Thr Gly Asp Lys Gly Arg Lys Ile Tyr
                565                 570                 575

Glu Trp Asp Ser Gln His Gly Glu Leu Glu Gly Tyr Arg Ala Ser Asp
            580                 585                 590

Gly Gln His Leu Gly Ser Phe Asp Pro Lys Thr Gly Asn Gln Leu Lys
        595                 600                 605

Gly Pro Asp Pro Lys Arg Asn Ile Lys Lys Tyr Leu
    610                 615                 620


<210> SEQ ID NO 52
<211> LENGTH: 395
<212> TYPE: PRT
<213> ORGANISM: Artificial Sequence
<220> FEATURE:
<223> OTHER INFORMATION: CHIMERIC PROTEIN: CYTOLETHAL DISTINDING TOXIN
      CLTDB FUSION WITH APOPTIN

<400> SEQUENCE: 52

Met Lys Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
            20                  25                  30

Ala Ser Ala Thr Thr Glu Ser Lys Trp Asn Ile Asn Val Arg Gln Leu
        35                  40                  45

Ile Ser Gly Glu Asn Ala Val Asp Ile Leu Ala Val Gln Glu Ala Gly
    50                  55                  60

Ser Pro Pro Ser Thr Ala Val Asp Thr Gly Thr Leu Ile Pro Ser Pro
65                  70                  75                  80

Gly Ile Pro Val Arg Glu Leu Ile Trp Asn Leu Ser Thr Asn Ser Arg
                85                  90                  95

Pro Gln Gln Val Tyr Ile Tyr Phe Ser Ala Val Asp Ala Leu Gly Gly
            100                 105                 110

Arg Val Asn Leu Ala Leu Val Ser Asn Arg Arg Ala Asp Glu Val Phe
        115                 120                 125

Val Leu Ser Pro Val Arg Gln Gly Gly Arg Pro Leu Leu Gly Ile Arg
    130                 135                 140

Ile Gly Asn Asp Ala Phe Phe Thr Ala His Ala Ile Ala Met Arg Asn
145                 150                 155                 160

Asn Asp Ala Pro Ala Leu Val Glu Glu Val Tyr Asn Phe Phe Arg Asp
                165                 170                 175

Ser Arg Asp Pro Val His Gln Ala Leu Asn Trp Met Ile Leu Gly Asp
            180                 185                 190

Phe Asn Arg Glu Pro Ala Asp Leu Glu Met Asn Leu Thr Val Pro Val
        195                 200                 205
```

```
Arg Arg Ala Ser Glu Ile Ile Ser Pro Ala Ala Ala Thr Gln Thr Ser
    210                 215                 220

Gln Arg Thr Leu Asp Tyr Ala Val Ala Gly Asn Ser Val Ala Phe Arg
225                 230                 235                 240

Pro Ser Pro Leu Gln Ala Gly Ile Val Tyr Gly Ala Arg Arg Thr Gln
                245                 250                 255

Ile Ser Ser Asp His Phe Pro Val Gly Val Ser Arg Arg Gly Gly Gly
            260                 265                 270

Gly Gly Met Asn Ala Leu Gln Glu Asp Thr Pro Pro Gly Pro Ser Thr
        275                 280                 285

Val Phe Arg Pro Pro Thr Ser Ser Arg Pro Leu Glu Thr Pro His Cys
    290                 295                 300

Arg Glu Ile Arg Ile Gly Ile Ala Gly Ile Thr Ile Thr Leu Ser Leu
305                 310                 315                 320

Cys Gly Cys Ala Asn Ala Arg Ala Pro Thr Leu Arg Ser Ala Thr Ala
                325                 330                 335

Asp Asn Ser Glu Ser Thr Gly Phe Lys Asn Val Pro Asp Leu Arg Thr
            340                 345                 350

Asp Gln Pro Lys Pro Pro Ser Lys Lys Arg Ser Cys Asp Pro Ser Glu
        355                 360                 365

Tyr Arg Val Ser Glu Leu Lys Glu Ser Leu Ile Thr Thr Thr Pro Ser
    370                 375                 380

Arg Pro Arg Thr Ala Lys Arg Arg Ile Arg Leu
385                 390                 395


<210> SEQ ID NO 53
<211> LENGTH: 370
<212> TYPE: PRT
<213> ORGANISM: Artificial Sequence
<220> FEATURE:
<223> OTHER INFORMATION: CHIMERIC PROTEIN: CYTOLETHAL DISTINDING TOXIN
      CLTDB FUSION WITH A TRUNCATED APOPTIN

<400> SEQUENCE: 53

Met Lys Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
            20                  25                  30

Ala Ser Ala Thr Thr Glu Ser Lys Trp Asn Ile Asn Val Arg Gln Leu
        35                  40                  45

Ile Ser Gly Glu Asn Ala Val Asp Ile Leu Ala Val Gln Glu Ala Gly
    50                  55                  60

Ser Pro Pro Ser Thr Ala Val Asp Thr Gly Thr Leu Ile Pro Ser Pro
65                  70                  75                  80

Gly Ile Pro Val Arg Glu Leu Ile Trp Asn Leu Ser Thr Asn Ser Arg
                85                  90                  95

Pro Gln Gln Val Tyr Ile Tyr Phe Ser Ala Val Asp Ala Leu Gly Gly
            100                 105                 110

Arg Val Asn Leu Ala Leu Val Ser Asn Arg Arg Ala Asp Glu Val Phe
        115                 120                 125

Val Leu Ser Pro Val Arg Gln Gly Gly Arg Pro Leu Leu Gly Ile Arg
    130                 135                 140

Ile Gly Asn Asp Ala Phe Phe Thr Ala His Ala Ile Ala Met Arg Asn
145                 150                 155                 160

Asn Asp Ala Pro Ala Leu Val Glu Glu Val Tyr Asn Phe Phe Arg Asp
                165                 170                 175
```

```
Ser Arg Asp Pro Val His Gln Ala Leu Asn Trp Met Ile Leu Gly Asp
            180                 185                 190

Phe Asn Arg Glu Pro Ala Asp Leu Glu Met Asn Leu Thr Val Pro Val
        195                 200                 205

Arg Arg Ala Ser Glu Ile Ile Ser Pro Ala Ala Ala Thr Gln Thr Ser
    210                 215                 220

Gln Arg Thr Leu Asp Tyr Ala Val Ala Gly Asn Ser Val Ala Phe Arg
225                 230                 235                 240

Pro Ser Pro Leu Gln Ala Gly Ile Val Tyr Gly Ala Arg Arg Thr Gln
                245                 250                 255

Ile Ser Ser Asp His Phe Pro Val Gly Val Ser Arg Arg Gly Gly Gly
            260                 265                 270

Gly Gly Ile Thr Pro His Cys Arg Glu Ile Arg Ile Gly Ile Ala Gly
        275                 280                 285

Ile Thr Ile Thr Leu Ser Leu Cys Gly Cys Ala Asn Ala Arg Ala Pro
    290                 295                 300

Thr Leu Arg Ser Ala Thr Ala Asp Asn Ser Glu Ser Thr Gly Phe Lys
305                 310                 315                 320

Asn Val Pro Asp Leu Arg Thr Asp Gln Pro Lys Pro Pro Ser Lys Lys
                325                 330                 335

Arg Ser Cys Asp Pro Ser Glu Tyr Arg Val Ser Glu Leu Lys Glu Ser
            340                 345                 350

Leu Ile Thr Thr Thr Pro Ser Arg Pro Arg Thr Ala Lys Arg Arg Ile
        355                 360                 365

Arg Leu
    370


<210> SEQ ID NO 54
<211> LENGTH: 288
<212> TYPE: PRT
<213> ORGANISM: Artificial Sequence
<220> FEATURE:
<223> OTHER INFORMATION: CHIMERIC PROTEIN: CYTOLETHAL DISTINDING TOXIN
      CLTDB FUSION WITH A TRUNCATED APOPTIN

<400> SEQUENCE: 54

Met Lys Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
            20                  25                  30

Ala Ser Ala Thr Thr Glu Ser Lys Trp Asn Ile Asn Val Arg Gln Leu
        35                  40                  45

Ile Ser Gly Glu Asn Ala Val Asp Ile Leu Ala Val Gln Glu Ala Gly
    50                  55                  60

Ser Pro Pro Ser Thr Ala Val Asp Thr Gly Thr Leu Ile Pro Ser Pro
65                  70                  75                  80

Gly Ile Pro Val Arg Glu Leu Ile Trp Asn Leu Ser Thr Asn Ser Arg
                85                  90                  95

Pro Gln Gln Val Tyr Ile Tyr Phe Ser Ala Val Asp Ala Leu Gly Gly
            100                 105                 110

Arg Val Asn Leu Ala Leu Val Ser Asn Arg Arg Ala Asp Glu Val Phe
        115                 120                 125

Val Leu Ser Pro Val Arg Gln Gly Gly Arg Pro Leu Leu Gly Ile Arg
    130                 135                 140

Ile Gly Asn Asp Ala Phe Phe Thr Ala His Ala Ile Ala Met Arg Asn
```

```
145                 150                 155                 160

Asn Asp Ala Pro Ala Leu Val Glu Glu Val Tyr Asn Phe Phe Arg Asp
                165                 170                 175

Ser Arg Asp Pro Val His Gln Ala Leu Asn Trp Met Ile Leu Gly Asp
            180                 185                 190

Phe Asn Arg Glu Pro Ala Asp Leu Glu Met Asn Leu Thr Val Pro Val
        195                 200                 205

Arg Arg Ala Ser Glu Ile Ile Ser Pro Ala Ala Ala Thr Gln Thr Ser
    210                 215                 220

Gln Arg Thr Leu Asp Tyr Ala Val Ala Gly Asn Ser Val Ala Phe Arg
225                 230                 235                 240

Pro Ser Pro Leu Gln Ala Gly Ile Val Tyr Gly Ala Arg Arg Thr Gln
                245                 250                 255

Ile Ser Ser Asp His Phe Pro Val Gly Val Ser Arg Arg Gly Gly Gly
            260                 265                 270

Gly Gly Ile Arg Ile Gly Ile Ala Gly Ile Thr Ile Thr Leu Ser Leu
        275                 280                 285


<210> SEQ ID NO 55
<211> LENGTH: 318
<212> TYPE: PRT
<213> ORGANISM: Artificial Sequence
<220> FEATURE:
<223> OTHER INFORMATION: CHIMERIC PROTEIN: CYTOLETHAL DISTINDING TOXIN
      CLTDB FUSION WITH A TRUNCATED APOPTIN

<400> SEQUENCE: 55

Met Lys Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
            20                  25                  30

Ala Ser Ala Thr Thr Glu Ser Lys Trp Asn Ile Asn Val Arg Gln Leu
        35                  40                  45

Ile Ser Gly Glu Asn Ala Val Asp Ile Leu Ala Val Gln Glu Ala Gly
    50                  55                  60

Ser Pro Pro Ser Thr Ala Val Asp Thr Gly Thr Leu Ile Pro Ser Pro
65                  70                  75                  80

Gly Ile Pro Val Arg Glu Leu Ile Trp Asn Leu Ser Thr Asn Ser Arg
                85                  90                  95

Pro Gln Gln Val Tyr Ile Tyr Phe Ser Ala Val Asp Ala Leu Gly Gly
            100                 105                 110

Arg Val Asn Leu Ala Leu Val Ser Asn Arg Arg Ala Asp Glu Val Phe
        115                 120                 125

Val Leu Ser Pro Val Arg Gln Gly Gly Arg Pro Leu Leu Gly Ile Arg
    130                 135                 140

Ile Gly Asn Asp Ala Phe Phe Thr Ala His Ala Ile Ala Met Arg Asn
145                 150                 155                 160

Asn Asp Ala Pro Ala Leu Val Glu Glu Val Tyr Asn Phe Phe Arg Asp
                165                 170                 175

Ser Arg Asp Pro Val His Gln Ala Leu Asn Trp Met Ile Leu Gly Asp
            180                 185                 190

Phe Asn Arg Glu Pro Ala Asp Leu Glu Met Asn Leu Thr Val Pro Val
        195                 200                 205

Arg Arg Ala Ser Glu Ile Ile Ser Pro Ala Ala Ala Thr Gln Thr Ser
    210                 215                 220
```

-continued

```
Gln Arg Thr Leu Asp Tyr Ala Val Ala Gly Asn Ser Val Ala Phe Arg
225                 230                 235                 240

Pro Ser Pro Leu Gln Ala Gly Ile Val Tyr Gly Ala Arg Arg Thr Gln
                245                 250                 255

Ile Ser Ser Asp His Phe Pro Val Gly Val Ser Arg Arg Gly Gly Gly
            260                 265                 270

Gly Gly Thr Asp Gln Pro Lys Pro Pro Ser Lys Lys Arg Ser Cys Asp
        275                 280                 285

Pro Ser Glu Tyr Arg Val Ser Glu Leu Lys Glu Ser Leu Ile Thr Thr
    290                 295                 300

Thr Pro Ser Arg Pro Arg Thr Ala Lys Arg Arg Ile Arg Leu
305                 310                 315


<210> SEQ ID NO 56
<211> LENGTH: 12
<212> TYPE: PRT
<213> ORGANISM: Artificial Sequence
<220> FEATURE:
<223> OTHER INFORMATION: SEQUENCE ASSOCIATED WITH DIMERIZATION AND
      INACTIVATION

<400> SEQUENCE: 56

Phe Arg Asp Ser Arg Asp Pro Val His Gln Ala Leu
1               5                   10


<210> SEQ ID NO 57
<211> LENGTH: 6
<212> TYPE: PRT
<213> ORGANISM: Artificial Sequence
<220> FEATURE:
<223> OTHER INFORMATION: FURIN CLEAVAGE SITE
<220> FEATURE:
<221> NAME/KEY: misc_feature
<222> LOCATION: (2)..(2)
<223> OTHER INFORMATION: Xaa can be any naturally occurring amino acid

<400> SEQUENCE: 57

Arg Xaa Arg Ala Lys Arg
1               5


<210> SEQ ID NO 58
<211> LENGTH: 12
<212> TYPE: PRT
<213> ORGANISM: Artificial Sequence
<220> FEATURE:
<223> OTHER INFORMATION: HAEMOPHILUS LOOP ASSOCIATED WITH STABLE
      RETENTION OF CYTOTOXICITY

<400> SEQUENCE: 58

Asn Ser Ser Ser Ser Pro Pro Glu Arg Arg Val Tyr
1               5                   10


<210> SEQ ID NO 59
<211> LENGTH: 33
<212> TYPE: PRT
<213> ORGANISM: Artificial Sequence
<220> FEATURE:
<223> OTHER INFORMATION: GASTRIN-34 (BIG GASTRIN)

<400> SEQUENCE: 59

Leu Gly Pro Gln Gly Pro Pro His Leu Val Ala Asp Pro Ser Lys Lys
1               5                   10                  15

Gln Gly Pro Trp Leu Glu Glu Glu Glu Glu Ala Tyr Gly Trp Met Asp
            20                  25                  30
```

-continued

```
Phe


<210> SEQ ID NO 60
<211> LENGTH: 9
<212> TYPE: PRT
<213> ORGANISM: Artificial Sequence
<220> FEATURE:
<223> OTHER INFORMATION: FURIN INHIBITOR

<400> SEQUENCE: 60

Gly Lys Arg Pro Arg Ala Lys Arg Ala
1               5
```